United States Patent
Castro Palomino Laria et al.

(10) Patent No.: US 10,744,125 B2
(45) Date of Patent: Aug. 18, 2020

(54) ADENOSINE A3 RECEPTOR MODULATORS

(71) Applicant: Palobiofarma, S.L., Mataró, Barcelona (ES)

(72) Inventors: Julio Castro Palomino Laria, Barcelona (ES); Juan Camacho Gómez, Barcelona (ES); Abdelaziz El Maatougui, Noáin-Navarra (ES)

(73) Assignee: Palobiofarma, S.L., Mataro, Barcelona (ES)

( * ) Notice: Subject to any disclaimer, the term of this patent is extended or adjusted under 35 U.S.C. 154(b) by 0 days.

(21) Appl. No.: 16/479,448

(22) PCT Filed: Jan. 19, 2018

(86) PCT No.: PCT/ES2018/070039
§ 371 (c)(1),
(2) Date: Jul. 19, 2019

(87) PCT Pub. No.: WO2018/134464
PCT Pub. Date: Jul. 26, 2018

(65) Prior Publication Data
US 2019/0374530 A1     Dec. 12, 2019

(30) Foreign Application Priority Data
Jan. 20, 2017   (ES) .................. 201730065

(51) Int. Cl.
*A61K 31/4545* (2006.01)
*A61K 31/167* (2006.01)
*A61K 31/352* (2006.01)
*A61K 31/366* (2006.01)
*A61K 31/40* (2006.01)
*A61K 31/47* (2006.01)
*A61K 31/505* (2006.01)
*A61K 31/519* (2006.01)
*A61K 31/549* (2006.01)
*C07D 417/14* (2006.01)

(52) U.S. Cl.
CPC ........ *A61K 31/4545* (2013.01); *A61K 31/167* (2013.01); *A61K 31/352* (2013.01); *A61K 31/366* (2013.01); *A61K 31/40* (2013.01); *A61K 31/47* (2013.01); *A61K 31/505* (2013.01); *A61K 31/519* (2013.01); *A61K 31/549* (2013.01); *C07D 417/14* (2013.01)

(58) Field of Classification Search
CPC ................................................. A61K 31/4545
USPC ....................................................... 546/193
See application file for complete search history.

(56) References Cited

U.S. PATENT DOCUMENTS

2003/0203897 A1   10/2003   Love et al.
2011/0171130 A1   7/2011    Jacobson et al.
2011/0190324 A1   8/2011    Leung et al.
2012/0053176 A1   3/2012    Armstrong et al.
2012/0134945 A1   5/2012    Madi et al.

FOREIGN PATENT DOCUMENTS

EP    1 180 518     2/2002
EP    1 983 990     3/2011

OTHER PUBLICATIONS

PCT International Patent Application Publication No. WO 99/21555 (Takeda Chemical Industries, Ltd. [JP/JP]), published May 6, 1999.
PCT International Patent Application Publication No. WO 99/64418 (Novartis AG [CH/CH]) published Dec. 16, 1999.
PCT International Patent Application Publication No. WO 00/03741 (The Trustees of the University of Pennsylvania [US/US]), published Jan. 27, 2000.
PCT International Patent Application Publication No. WO 00/15321 (Medco Research Inc. [US/US]), published Mar. 23, 2000.
PCT International Patent Application Publication No. WO 2005/009969 (Sanofiaventis [FR/FR]), published Feb. 3, 2005.
PCT International Patent Application Publication No. WO 2007/116106, (Palobiofarma, S.L., [ES/ES]), published Oct. 18, 2007.
PCT International Patent Application Publication No. WO 2008/006369 (Santaris Pharma A/S, [DK/DK]), published Jan. 17, 2008.
PCT International Patent Application Publication No. WO 2008/045330 (The Trustees of the University of Pennsylvania [US/US]), published Apr. 17, 2008.
PCT International Patent Application Publication No. WO 2009/044250 (Palobiofarma, S.L. [ES/ES]), published Apr. 9, 2009.
PCT International Patent Application Publication No. WO 2009/052310 (CV Therapeutics, Inc. [US/US]), published Apr. 23, 2009.
PCT International Patent Application Publication No. WO 2016/116652 (Palobiofarma, S.L. [ES/ES]), published Jul. 28, 2016.
Antipas, A. et al., "Structure-activity relationships and hepatic safety risks of thiazole agonists of the thrombopoietin receptor", Bioorganic & Medicinal Chemistry.
Bar-Yehuda, S. et al, "The anti-inflammatory effects of $A_3$ adenosine receptor agonists: a novel targeted therapy for rheumatoid arthritis", Expert Opinion on Investigational Drugs, vol. 16, No. 10, 2007, pp. 1601-1613.

(Continued)

*Primary Examiner* — Taofiq A Solola
(74) *Attorney, Agent, or Firm* — Gary J. Gershik; Cooper & Dunham LLP

(57) ABSTRACT

Modulators of the adenosine $A_3$ receptors of formula (I):

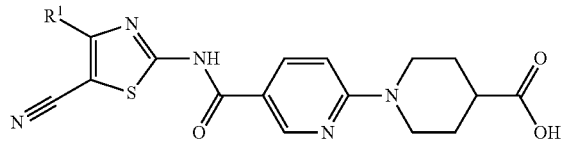

and process for preparing said compounds. Other aspects of the present invention are pharmaceutical compositions comprising an effective amount of said compounds and the use of said compounds in the preparation of a medicament for treating pathological conditions or diseases that can be improved by modulation of adenosine $A_3$ receptors.

12 Claims, No Drawings

(56) References Cited

OTHER PUBLICATIONS

Bar-Yehuda, S. et al, "Inhibition of experimental auto-immune uveitis by the $A_3$ adenosine receptor agonist CF101", International Journal of Molecular Medicine, vol. 28, 2011, pp. 727-773.

Baraldi, P.G. et al., "Medicinal Chemistry of $A_3$ Adenosine Receptor Modulators: Pharmacological Activities and Therapeutic Implications", Journal of Medicinal Chemistry, vol. 55, 2012, pp. 5676-5703.

Boison, D., "Adenosine-Based Modulation of Brain Activity", Current Neuropharmacology, 2009, vol. 7, No. 3, 158-159.

Borea, P.A. et al., "The $A_3$ Adenosine Receptor: History and Perspectives", Pharmacological Reviews, vol. 67, 2015, pp. 74-102.

Braselmann, S. et al., "R406, an Orally Available Spleen Tyrosine Kinase Inhibitor Blocks Fc Receptor Signaling and Reduces Immune Complex-Mediated Inflammation", The Journal of Pharmacology and Experimental Therapeutics, vol. 319, No. 3, 2006, pp. 998-1008.

Burnstock, G. et al., "Adenosine and ATP Receptors in the Brain", Current Topics in Medicinal Chemistry, vol. 11, 2011, pp. 973-1011.

Butler, M., et al., "Impairment of adenosine A3 receptor activity disrupts neutrophil migratory capacity and impacts innate immune function in vivo", European Journal of Immunology, vol. 42, 2012, pp. 3358-3368.

De Schepper, H.U. et al., "Review article: gastrointestinal sensory and motor disturbances in inflammatory bowel disease—clinical relevance and pathophysiological mechanisms", Alimentary Pharmacology & Therapeutics, vol. 27, 2008, pp. 621-637.

Fredholm, B.B. et al., "International Union of Pharmacology. XXV. Nomenclature and Classification of Adenosine Receptors", Pharmacological Reviews, vol. 53, No. 4, 2001, pp. 527-552.

Gessi, S. et al., "Adenosine Receptors in Colon Carcinoma Tissues and Colon Tumoral Cell Lines: Focus on the $A_3$ Adenosine Subtype", Journal of Cellular Physiology, vol. 211, 2007, pp. 826-836.

Gessi, S. et al., "Adenosine Modulates HIF-1α, VEGF, IL-8, and Foam Cell Formation in a Human Model of Hypoxic Foam Cells", Arterioscler Thromb Vasc Biol, vol. 30, 2010, pp. 90-97.

Hanauer, S.B. and Present, D.H., "The State of the Art in the Management of Inflammatory Bowel Disease", Reviews in Gastroenterological Disorders, vol. 3, No. 2, 2003, pp. 81-92.

Jajoo, S. et al., "Adenosine $A_3$ Receptor Suppresses Prostate Cancer Metastasis by Inhibiting NADPH Oxidase Activity[1,2]", Neoplasia, vol. 11, No. 11, 2009, pp. 1132-1145.

Koscsó, B. et al., "Investigational $A_3$ adenosine receptor targeting agents", Expert Opinion Investig Drugs, vol. 20, No. 6, 2011, pp. 757-768.

Lee, H.T. et al., "$A_3$ adenosine receptor knockout mice are protected against ischemia- and myoglobinuria-induced renal failure", Am J Physiol Renal Physiol, vol. 284, 2003, pp. F267-F273.

Mabley, J. et al., "The adenosine $A_3$ receptor agonist, $N^6$-(3-iodobenzyl)-adenosine-5'-N-methyluronamide, is protective in two murine models of colitis", European Journal of Pharmacology, vol. 466, 2003, pp. 323-329.

Maddock. H.L. et al., "Adenosine $A_3$ receptor activation protects the myocardium from reperfusion/reoxygenation injury", Am J Physiol Heart Circ Physiol, vol. 283, 2002, pp. H1307-H1313.

Miwatashi, S. et al., "Synthesis and Biological Activities of 4-Phenyl-5-pyridyl-1,3-thiazole Derivatives as Selective Adenosine $A_3$ Antagonists", Chem. Pharm. Bull., vol. 56, No. 8, 2008, pp. 1126-1137.

Mócsai, A. et al., "The SYK tyrosine kinase: a crucial player in diverse biological functions", Nature Reviews Immunology, vol. 10, 2010, pp. 387-402.

Ochaion, A. et al., "The anti-inflammatory target $A_3$ adenosine receptor is over-expressed in rheumatoid arthritis, psoriasis and Crohn's disease", Cellular Immunology, vol. 258, 2009, pp. 115-122.

Pugliese, A.M. et al., "Brief, repeated, oxygen-glucose deprivation episodes protect neurotransmission from a longer ischemic episode in the in vitro hippocampus: role of adenosine receptors", British Journal of Pharmacology, vol. 140, 2003, pp. 305-314.

Ren, T. et al., "Impact of Disrupting Adenosine $A_3$ Receptors ($A_3$-/-AR) on Colonic Motility or Progression of Colitis in the Mouse", Inflamm Bowel Dis., vol. 17, No. 8, 2011, pp. 1698-1713.

Salvatore, C.A. et al., "Disruption of the $A_3$ Adenosine Receptor Gene in Mice and Its Effect on Stimulated Inflammatory Cells", The Journal of Biological Chemistry, vol. 275, No. 6, 2000. pp. 4429-4434.

Schlötzer-Schrehardt, U. et al., "Selective Upregulation of the A3 Adenosine Receptor in Eyes with Pseudoexfoliation Syndrome and Glaucoma", Investigative Ophthalmology & Visual Science, vol. 46, No. 6, 2005, pp. 2023-2034.

Silverman, M.H. et al., "Clinical Evidence for Utilization of the $A_3$ Adenosine Receptor as a Target to Treat Rheumatoid Arthritis: Data from a Phase II Clinical Trial", The Journal of Rheumatology, vol. 35, No. 1, 2008, pp. 1-8.

Van der Hoeven D. et al., "Activation of the $A_3$ Adenosine Receptor Suppresses Superoxide Production and Chemotaxis of Mouse Bone Marrow Neutrophils", Molecular Pharmacology, vol. 74, No. 3, 2008, pp. 685-696.

Von Arnim C.A.F. et al., "GGA1 Acts as a Spatial Switch Altering Amyloid Precursor Protein Trafficking and Processing", The Journal of Neuroscience, vol. 26, No. 39, 2006, pp. 9913-9922.

Yang, H. et al., "The Cross-Species $A_3$ Adenosine-Receptor Antagonist MRS 1292 Inhibits Adenosine-Triggered Human Nonpigmented Ciliary Epithelial Cell Fluid Release and Reduces Mouse Intraocular Pressure", Current Eye Research, vol. 30, 2005, pp. 747-754.

Yoon, M.H. et al., "Roles of Adenosine Receptor Subtypes in the Antinociceptive Effect of Intrathecal Adenosine in a Rat Formalin Test", Pharmacology, vol. 78, 2006, pp. 21-26.

Young, H.W.J. et al, "$A_3$ Adenosine Receptor Signaling Contributes to Airway Inflammation and Mucus Production in Adenosine Deaminase-Deficient Mice[1]" The Journal of Immunology, vol. 173, 2004, pp. 1380-1389.

Zhang, M. et al., "The $A_3$ adenosine receptor attenuates the calcium rise triggered by NMDA receptors in retinal ganglion cells", Neurochemistry International, vol. 56, 2010, pp. 35-41.

Zhong, H. et al., "Activation of Murine Lung Mast Cells by the Adenosine $A_3$ Receptor", The Journal of Immunology, vol. 170, 2003, pp. 338-345.

Zhong, Y. et al., "Adenosine, adenosine receptors and glaucoma: An updated overview", Biochimica et Biophysica Acta, vol. 1830, 2013, pp. 2882-2890.

ADENOSINE A3 RECEPTOR MODULATORS

RELATED APPLICATIONS

This application is a § 371 national stage of PCT International Application No. PCT/ES2018/070039, filed Jan. 19, 2018, claiming priority of Spanish Patent Application P201730065, filed Jan. 20, 2017, the contents of each of which are hereby incorporated by reference into this application.

FIELD OF THE INVENTION

The present invention relates 1-(5-(thyazol-2-ylcarbamoyl)pyridin-2-yl)pyperidin-4-carboxylic acid derivatives as adenosine $A_3$ receptor modulators. Other aspects of the present invention are a procedure for preparing these compounds; pharmaceutical compositions comprising an effective amount of these compounds; the use of the compounds for manufacturing a medicament for the treatment of pathological conditions or diseases that can improve by modulation of the adenosine $A_3$ receptor.

STATE OF THE ART

The effects of adenosine are mediated through at least four specific membrane receptors that are classified as $A_1$, $A_{2A}$, $A_{2B}$ and $A_3$ receptors and belong to the family of G protein coupled receptors. The $A_1$ and $A_3$ receptors decreases intracellular levels of cyclic adenosine monophosphate (cAMP) by coupling to inhibitory G proteins (Gi) to inhibit the enzyme adenylate cyclase. In contrast, the $A_{2A}$ and $A_{2B}$ receptors stimulatory G proteins (Gs) to activate adenylate cyclase and increase intracellular cAMP levels are coupled. Through these receptors, adenosine regulates a wide range of physiological functions.

Adenosine $A_3$ Receptors in Gastrointestinal Disorders

Ulcerative colitis and Crohn's disease, collectively known as inflammatory bowel disease, are severe and debilitating disorders with a growing incidence in both developing and advanced countries. (Hanauer, S. B.; Present, D. H. *The state of the art in the management of inflammatory bowel disease*. Rev. Gastroenterol. Disord. 2003, 3, 81-92).

Both diseases are characterized by serious inflammation of the enteric mucosa at different levels of the gastrointestinal tract associated with significant alterations of gastrointestinal motor, secretory, and sensory functions. (De Schepper, H. U.; De Man, J. G.; Moreels, T. G.; Pelckmans, P. A.; De Winter, B. Y. *Review article: gastrointestinal sensory and motor disturbances in inflammatory bowel disease: clinical relevance and pathophysiological mechanisms*. Aliment. Pharmacol. Ther. 2008, 27, 621-637).

Modulators of adenosine $A_3$ receptors are being studied as emerging treatments of bowel inflammation.

Recently it has been confirmed that adenosine $A_3$ ($A_3ARs$) receptors are up-regulated in various autoimmune diseases such as Crohn's disease, rheumatoid arthritis and psoriasis if compared with healthy subjects, whereby said receptor has been considered an important target to treat such autoimmune inflammatory diseases. (Ochaion, A et al. *The anti-inflammatory target A(3) adenosine receptor is over-expressed in rheumatoid arthritis, psoriasis and Crohn's disease*. Cell Immunol. 2009; 258(2):115-22. doi: 10.1016/j.cellimm.2009.03.020. Epub 2009 May 7).

The known $A_3AR$ agonist, IB-MECA, was used in mice to ameliorate intestinal inflammation and spontaneous colitis. In addition, $A_3AR$ stimulation was able to markedly reduce colonic levels of proinflammatory cytokines such as IL-1, IL-6 and IL-12. (Mabley, J. et al, *The adenosine A3 receptor agonist, N6-(3-iodobenzyl)-adenosine-5'-N-methyluronamide, is protective in two murine models of colitis*. Eur. J. Pharmacol. 2003, 466, 323-329).

Furthermore, a recent study has demonstrated the role of $A_3AR$ in colonic motility and progression of colitis in mouse model induced disease—with dextran sulphate sodium (DSS)—, showing $A_3AR$ knockout mouse model ($A_3$−/− AR) develops fewer symptoms or recover faster than that have the receptor (wild type). The data obtained suggest that activation of $A_3AR$ by endogenous adenosine slows-down intestinal transit, colonic emptying and mass movement in mouses, supporting the hypothesis that the activation of this receptor contributes to the development of colitis. (Tianhua Ren, M D, et al. *Impact of Disrupting Adenosine $A_3$ Receptors ($A_3$−/−AR) on Colonic Motility or Progression of Colitis in the Mouse*. Inflamm Bowel Dis. 2011, August; 17(8): 1698-1713).

Subsequently other studies have indicated that adenosine $A_3$ receptor deficient mice showed reduced colon pathology and decreased levels of myeloperoxidase enzyme, and evidenced the role of $A_3AR$ in neutrophil migration, showing that the alteration of this function has the potential to affect negatively the innate immune response. (Butler, M et al. *Impairment of adenosine $A_3$ receptor activity disrupts neutrophil migratory capacity and impacts innate immune function in vivo*. European Journal of Immunology. Sep. 26, 2012).

Adenosine $A_3$ Receptors in the Central Nervous System $A_3ARs$ are widely distributed in the central nervous system but at low levels and with a reduced affinity. The role of $A_3ARs$ in several pathophysiological conditions is often controversial, although there are signs that point to an important role of these receptors in neurotransmission. (Boison, D. *Adenosine as a modulator of brain activity*. Drug News Perspect. 2007, 20, 607-611; Burnstock, G. et al, *Adenosine and ATP receptors in the brain*. Curr. Top. Med. Chem. 2011, 11, 973-1011).

It has been reported that $A_3AR$ agonists have depressant effects on locomotor activity, suggesting a possible inhibition of excitatory neurotransmission in cortical neurons. (Boison, D. *Adenosine as a modulator of brain activity*. Drug News Perspect. 2007, 20, 607-611).

Furthermore, a nociceptive role for $A_3ARs$ involving both central nervous system and proinflammatory effects in peripheral tissues has been highlighted. (Yoon, M. H. et al, *Roles of adenosine receptor subtypes in the antinociceptive effect of intrathecal adenosine in a rat formalin test*. Pharmacology 2006, 78, 21-26).

The role of $A_3ARs$ in neurodegenerative phenomena emerges from studies performed in vivo and in vitro models of hypoxia/ischemia. It has been hypothesized that $A_3ARs$ play a protective role in the first phase of ischemia by decreasing synaptic transmission. (Pugliese, A. M. et al, *Brief, repeated, oxygen-glucose deprivation episodes protect neurotransmission from a longer ischemic episode in the in vitro hippocampus: role of adenosine receptors*. Br. J. Pharmacol. 2003, 140, 305-314).

In addition, an up-regulation of $A_3ARs$ in the hippocampus of a transgenic mouse model of Alzheimer's disease has been reported, where an altered oxidative phosphorylation was detected prior to amyloid deposition. (von Arnim, C. A. et al, *GGA1 acts as a spatial switch altering amyloid precursor protein trafficking and processing*. J. Neurosci. 2006, 26, 9913-9922).

Finally, different studies have evaluated the role of the adenosine $A_3$ receptor in stages of pain. Some of them have demonstrated a nociceptive and proinflammatory response that causes the formation of edema, due to the activation of this receptor. However, an opposite activity in pain modulation has been observed in later studies; suggesting a potential application for adenosine $A_3$ receptor agonists in the treatment of chronic neuropathic pain, since agonists of said receptor block the development of mechanically induced neuropathic pain and chemotherapy in a dose-dependent manner and significantly increase the analgesic effects of various currently used analgesic drugs. (Borea, P A et al, *The $A_3$ Adenosine Receptor: History and Perspectives*, Pharmacol Rev 67:74-102, January 2015, and references therein).

Adenosine $A_3$ Receptors in Renal Disorders

There are published studies showing the harmful effects that can have $A_3AR$ activation in renal ischemia. In a study conducted in a model of induced renal failure in mice, an $A_3AR$ antagonist has been shown to improve blood parameters such as blood urea and creatinine, as well as decreased morphological damage in the kidney, compared to effects obtained when using IB-MECA, which proved to be harmful. (Koscsó, B et al. *Investigational $A_3$ adenosine receptor targeting agents*. Expert Opin Investig Drugs. 2011 June; 20(6): 757-768. doi:10.1517/13543784.2011.573785 and references therein).

In another study conducted in mouse model of renal ischemia similar results were obtained, checking that renal failure was attenuated both $A_3AR$ receptor deficient mice, as well in mice (wild type) previously treated with an antagonist of said adenosine $A_3$ receptor. (Thomas Lee, H et al. *$A_3$ adenosine receptor knockout mice are protected against ischemia-and myoglobinuria-induced renal failure*. Am J Physiol Renal Physiol. 2003. 284: F267-F273).

Adenosine $A_3$ Receptors in Cardiovascular System

It is also reported that $A_3ARs$ mediate vascular protection and contribute to limitations in infarct size and in post ischemic myocardium by a mechanism that involves PKC, KATP channel activation, phosphorylation of p38MAPKs, and glycogen synthase kinase. (Maddock, H. L et al, *Adenosine $A_3$ receptor activation protects the myocardium from reperfusion/reoxygenation injury*. Am. J. Physiol.: Heart Circ. Physiol. 2002, 283, H1307-H1313).

Atherosclerosis, a multifactorial disease of the large arteries, is the major cause of heart disease and stroke worldwide. Epidemiological studies have discovered several relevant environmental and genetic risk factors associated with this pathology. Most recently, it has been shown that adenosine through the activation of $A_3ARs$ stimulates VEGF secretion and stimulates foam cell formation, and this effect is strongly reduced by $A_3AR$ antagonists.

So, as a consequence, the potential use of $A_3AR$ antagonists could be of interest to block important steps in the atherosclerotic plaque development. (Gessi, S.; Foet et al, *Adenosine modulates HIF-1{alpha}}, VEGF, IL-8, and foam cell formation in a human model of hypoxic foam cells*. Arterioscler., Thromb., Vasc. Biol. 2010, 30, 90-97).

Adenosine $A_3$ Receptors in Immune System $A_3ARs$ are present in immune cells and are involved in the pathophysiological regulation of inflammatory and immune processes. Several results from in vitro and in vivo studies suggest that the activation of $A_3ARs$ can be both pro- or anti-inflammatory depending on the cell type examined or on the animal species considered. (Baraldi P G et al, *Medicinal Chemistry of A3 Adenosine Receptor Modulators: Pharmacological Activities and Therapeutic Implications*, J. Med. Chem. 2012, 55, 5676-5703, and references therein). Functional studies have shown that human neutrophils expressed $A_3ARs$, mediating the inhibition of oxidative burst. (van der Hoeven, D. et al, *Activation of the $A_3$ adenosine receptor suppresses superoxide production and chemotaxis of mouse bone marrow neutrophils*. Mol. Pharmacol. 2008, 74, 685-696).

There are evidences that $A_3ARs$ are present in human eosinophils, coupled to signalling pathways of cellular activation, and are able to protect eosinophils from apoptosis and inhibit the chemotaxis process. An overexpression of $A_3AR$ has also been detected in lymphocytes and in Jurkat cells, a human leukemic cell line, being associated with the inhibition of the activity of the enzyme adenylate cyclase and calcium modulation. In macrophages, the activation of $A_3AR$ seems to indicate an anti-inflammatory effect of same. (Baraldi P G et al, *Medicinal Chemistry of $A_3$ Adenosine Receptor Modulators: Pharmacological Activities and Therapeutic Implications*, J. Med. Chem. 2012, 55, 5676-5703, and references therein).

In addition, others evidences point out to the implication of $A_3AR$ in autoimmune diseases, where there has been an overexpression of these receptors in several pathologies of this type. Among these diseases are rheumatoid arthritis, Crohn's disease and psoriasis, among others. (Braselmann S. et al, *R406, an Orally Available Spleen Tyrosine Kinase Inhibitor Blocks Fc Receptor Signaling and Reduces Immune Complex-Mediated Inflammation*, The Journal of Pharmacology and Experimental Therapeutics, Vol. 319, No. 3).

Others studies point out to the role of $A_3AR$ in diseases such as immune thrombocytopenia (ITP), since it has been proven that prodrug fostamatinib, which is a SYK tyrosine kinase inhibitor and is in clinical phase III for the treatment of ITP, has an important affinity on the $A_3AR$ receptor ($IC_{50}$=81 nM), in addition to activity in other immune signaling pathways, reason why it has been considered that this SYK tyrosine kinase inhibitor performs its clinical effects through other pathways of signaling independent of the SYK tyrosine kinase, as is the $A_3AR$ receptor pathway. (Mócsai A. et al, *The SYK tyrosine kinase: a crucial player in diverse biological functions*, Nature Reviews—Immunology Volume 10, June 2010).

Adenosine $A_3$ Receptors in Rheumatoid Arthritis

Clinical evidence in rheumatoid arthritis (RA) patients shows that treatment with an adenosine $A_3$ receptor agonist leads to an improvement in signs and symptoms of disease. (Silverman, M. H. et al, *Clinical evidence for utilization of the A3 adenosine receptor as a target to treat rheumatoid arthritis: data from a phase II clinical trial*. J. Rheumatol. 2008, 35, 41-48).

The overexpression of $A_3ARs$ in RA has been directly correlated to high levels of proinflammatory cytokines, acting via an upregulation of NF-kB, which is a key player in the pathogenesis of arthritic diseases. (Bar-Yehuda, S. et al, *The anti-inflammatory effect of A3 adenosine receptor agonists: a novel targeted therapy for rheumatoid arthritis*. Expert Opin. Invest. Drugs 2007, 16, 1601-1613).

In a phase II clinical study in RA patients, IB-MECA (1-deoxy-1-[6-[((3-iodophenyl)methyl)amino]-9H-purin-9-yl]-N-methyl-β-D-ribofuranuronamide) oral administration twice daily for 12 weeks was shown to be safe, well tolerated and able to mediate an improvement of disease signs and symptoms, suggesting the development of $A_3$ adenosine receptor modulators as antirheumatic agents.

Adenosine $A_3$ Receptors in Respiratory Tract

The role of adenosine in regulating the respiratory system is well-known, and elevated levels of adenosine have been found in bronchoalveolar lavage (BAL), blood and exhaled breath condensate of patients with asthma, and chronic obstructive pulmonary disease (COPD).

$A_3ARs$ have been implicated in inflammatory processes, playing an important role in both pro- or anti-inflammatory responses, strictly depending on different cell type involved. (Salvatore, C. A. et al, *Disruption of the $A_3$ adenosine receptor gene in mice and its effect on stimulated inflammatory cells*. J. Biol. Chem. 2000, 275, 4429-4434).

In particular, the strongest evidence of an $A_3AR$ functional role in mast cell activation comes from the use of genetic knockout mice where the mast cell degranulation in the absence or in the presence of allergen appears to be dependent on adenosine receptor activation (Zhong, H.; et al, *Activation of murine lung mast cells by the adenosine $A_3$ receptor*. J. Immunol. 2003, 171, 338-345).

The airway hyperresponsiveness is diminished in $A_3AR$ deficient mice, therefore mice treated with selective $A_3AR$ antagonists showed a marked attenuation of pulmonary inflammation, reduced eosinophil infiltration into the airways, and decreased airway mucus production. (Young, H. W. et al, *$A_3$ adenosine receptor signalling contributes to airway inflammation and mucus production in adenosine deaminase-deficient mice*. J. Immunol. 2004, 173, 1380-1389).

These data suggest the potential use of antagonists of adenosine $A_3$ receptor in conditions related to lung diseases in which inflammation is an important feature.

Adenosine $A_3$ Receptors in Eye Disease

Modulating adenosine $A_3$ receptors as potential therapeutic target for the treatment of various eye diseases such as dry eye syndrome, glaucoma or uveitis has been reported (Y. Zhong, et al., Adenosine, adenosine receptors and glaucoma: An updated overview, Biochim. Biophys. Acta, 2013).

Early studies demonstrated that deletion of adenosine $A_3$ receptors in mice showed a reduction of intraocular pressure, suggesting that $A_3AR$ antagonists may represent a new therapy for glaucoma. (Yang, H. et al, *The cross-species adenosine-receptor antagonist MRS 1292 inhibits adenosine-triggered human nonpigmented ciliary epithelial cell fluid release and reduces mouse intraocular pressure*. Curr. Eye Res. 2005, 30, 747-754).

Moreover, $A_3AR$ mRNA and protein have been found to be consistently increased in the nonpigmented ciliary epithelium of the eye in pseudoexfoliation syndrome with glaucoma, compared to normal eye. (Schlotzer-Schrehardt, U. et al, *Selective upregulation of the $A_3$ adenosine receptor in eyes with pseudoexfoliation syndrome and glaucoma*. Invest. Ophthalmol. Visual Sci. 2005, 46, 2023-2034).

$A_3AR$ overexpression in retinal ganglion cells has also been reported. (Zhang, M.; et al, *The $A_3$ adenosine receptor attenuates the calcium rise triggered by NMDA receptors in retinal ganglion cells*. Neurochem. Int. 2010, 56, 35-41).

The anti-inflammatory and protective effects mediated via $A_3AR$ prompted to examine the effect of IB-MECA in a model of experimental autoimmune uveitis that represents human uveitis with an autoimmune etiology. In this model, IB-MECA inhibited the clinical and pathological manifestations of uveitis. (Bar-Yehuda, S.; et al, *Inhibition of experimental auto-immune uveitis by the $A_3$ adenosine receptor agonist CF101*. Int. J. Mol. Med. 2011, 28, 727-731).

Adenosine $A_3$ Receptors in Oncologic Disease $A_3ARs$ are present in different types of tumor cells, such as HL60 and K562 human leukemia, lymphoma, human glioblastoma and in human prostatic cells.

$A_3AR$ are involved in tumor growth and in cell cycle regulation. (Gessi, S.; et al, *Adenosine receptors in colon carcinoma tissues and colon tumoral cell lines: focus on the $A_3$ adenosine subtype*. J. Cell. Physiol. 2007, 211, 826-836).

In particular, the activation of the $A_3ARs$ in prostate cancer cells reducing PKA-mediated stimulation of ERK1/2, and leading to reduce cancer has been reported. (Jajoo, S.; et al, *Adenosine $A_3$ receptor suppresses prostate cancer metastasis by inhibiting NADPH oxidase activity*. Neoplasia 2009, 11, 1132-1145).

These data suggest that $A_3ARs$ could represent a biological marker and that $A_3AR$ modulation could be used in cancer treatment.

In patent literature are also described different applications related to modulators of adenosine $A_3$ receptor. For example, US 2003203897 discloses derivatives of 2,4 disubstituted thiazole having inhibitory properties on the production of pro-inflammatory cytokines and inhibition of said adenosine $A_3$ receptor.

Patent application WO 9921555 discloses compounds 1,3-azole derivatives as antagonists of adenosine $A_3$ receptor and its use as a prophylactic or therapeutic agent for treating asthma, allergies and inflammation, among others.

The document WO 9964418 discloses pyridyl aryl-thiazole as inhibitors of the adenosine $A_3$ receptor and its use as anti-inflammatory agents.

Patent application US 2012134945 discloses the use of antagonists of adenosine $A_3$ receptor in modulate production, secretion and/or accumulation of melanin, as well as methods of treating conditions such as skin hyperpigmentation.

Patent application US 2011190324 discloses the use of antagonists of adenosine $A_3$ receptor for the treatment of atherosclerosis and the combination of such antagonists with other anti-atherosclerotic agents.

Patent application US 2011171130 discloses the use of adenosine $A_3$ receptor antagonists and/or partial agonists for the treatment of numerous diseases, including cancer, inflammatory diseases, asthma, and glaucoma, among others.

Moreover, regarding the treatment of glaucoma and reduction of intraocular pressure in general, several patent documents disclosing different types of antagonists of the adenosine $A_3$ receptor, for example in WO 0003741, WO 2008045330 and US 2012053176.

Other patent documents contained in the prior art, such as WO2009052310, WO2008006369, EP1180518, ES2360632 and ES2204262 disclose the use of different types of adenosine $A_3$ receptor antagonists for the treatment of conditions such as neurological and cardiac ischemia, leukopenia, neutropenia, rheumatoid arthritis, multiple sclerosis, gastrointestinal disorders, respiratory disorders such as asthma and nervous system diseases, such as Alzheimer's disease, Huntington's disease and Parkinson's disease, among others.

Particularly in patent application WO 2005009969, it is mentioned that many antagonists of adenosine $A_3$ receptor disclosed in the literature belong to groups of flavonoids, 1,4-dihydropyridine derivatives, triazoloquinazolines, thyazolopyrimidines thyazolonaphthyridines and having a strong lipophilicity, making them poorly soluble in water. This feature hinders the in vivo applicability of such compounds. Therefore, compounds modulators of adenosine $A_3$ receptor soluble in water are desirable.

The authors of the present invention have found new 1-(5-(thyazol-2-ylcarbamoyl)pyridin-2-yl)pyperidin-4-carboxylic acid derivatives as $A_3$ adenosine receptor potent and selective modulators. Therefore, the present patent application discloses novel carboxylic acid derivatives as potent and selective adenosine $A_3$ receptor modulators.

SUMMARY OF THE INVENTION

In one of its aspects, the present invention refers to 1-(5-(thyazol-2-ylcarbamoyl)pyridin-2-yl)pyperidin-4-carboxylic acid derivatives of formula (I):

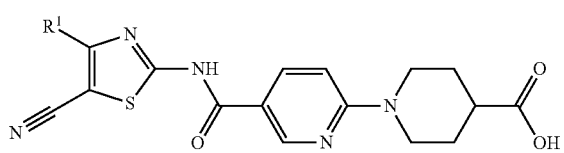

(I)

wherein:
$R^1$ represents a phenyl group or a five or six-membered heteroaryl group optionally substituted by 1, 2 or 3 substituents selected from the group consisting of halogen atom, $C_1$-$C_6$ haloalkyl linear or branched, $C_1$-$C_6$ alkyl linear or branched, $C_1$-$C_6$ alkoxy linear or branched and cyano group, Other aspects of the present invention are:
a) pharmaceutically acceptable salts thereof,
b) pharmaceutical composition comprising an effective amount of said compounds or its pharmaceutically acceptable salts,
c) the use of said compounds in the manufacture of a medicament for treating diseases that can be ameliorated by modulation of adenosine $A_3$ receptor selected from the group consisting of atherosclerosis, asthma, prostate cancer, acute renal failure, rheumatoid arthritis, psoriasis, immune thrombocytopenia, Crohn's disease, colitis, irritable bowel syndrome, glaucoma, dry eye syndrome, uveitis and neuropathic pain.
d) procedures for the treatment a disease that can be ameliorated by modulation of adenosine $A_3$ receptor as cardiovascular disease such as atherosclerosis, asthma, prostate cancer, acute renal failure, rheumatoid arthritis, psoriasis, immune thrombocytopenia, Crohn's disease, colitis, irritable bowel syndrome, glaucoma, dry eye syndrome, uveitis and neuropathic pain, comprising said procedures the administration of compounds of the present invention to a subject in need of treatment, and
e) combination comprising a compound of formula (I) according to the invention and other therapeutic agent, wherein said therapeutic agent is selected from agents for treating atherosclerosis, asthma, prostate cancer, acute renal failure, rheumatoid arthritis, psoriasis, immune thrombocytopenia, Crohn's disease, colitis, irritable bowel syndrome, glaucoma, dry eye syndrome, uveitis and neuropathic pain. The therapeutic agent is selected from the group consisting of inhibitors of 3-hydroxy-3-methyl-glutaryl-CoA reductase (HMG-CoA reductase) also known as statins including atorvastatin, rosuvastatin and simvastatin, leukotriene receptor antagonists such as Montelukast, gonadotropin releasing hormone (GnRH) agonist such as Bicalutamide, antiandrogen drugs such as Flutamide, inhibitors of Janus-kinase 1 and 3 (JAK 1 and 3) enzymes such as Tofacitinib, diuretic agents such as Hydrochlorothiazide and activators of secretion of intestinal fluids such as Lubiprostone. Preferably the additional therapeutic agent is selected from the group consisting of atorvastatin, rosuvastatin, simvastatin, Montelukast, Bicalutamide, Flutamide, Tofacitinib, Hydrochlorothiazide and Lubiprostone.

As used in the present patent application, the term $C_1$-$C_6$ alkyl group is used to design ($C_nH_{2n+1}$) hydrocarbons radicals, linear or branched, optionally substituted, having 1 to 6 carbon atoms. In an embodiment of present invention alkyl groups contain preferably 1 to 4 carbon atoms. The examples included the following radicals: methyl, ethyl, n-propyl, n-butyl, sec-butyl and terc-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl and iso-hexyl.

As used in the present patent application, the term $C_1$-$C_6$ alkoxy group is used to design radicals containing $C_1$-$C_6$ alkyl group linked to an oxygen atom ($C_2H_{2n+1}$—O—), linear or branched, optionally substituted, having 1 to 6 carbon atoms. In an embodiment of present invention alkoxy groups contain preferably 1 to 4 carbon atoms. Preferred alkoxy radicals are: methoxy, ethoxy, n-propoxy, i-propoxy, n-butoxy, sec-butoxy, t-butoxy, trifluoromethoxy, difluoromethoxy, hydroxymethoxy, 2-hydroxyethoxy or 2-hydroxypropoxy.

As used herein, the term heteroaryl group is used to design a five or six-membered ring with one, two or three heteroatoms selected from O, S and N. The heteroaryl group in the present invention can be optionally substituted. In an embodiment of the present invention, the preferred heteroaryl group are thienyl, furyl, pyridyl and thiazolyl. When a heteroaryl group has two or more substituents, they may be the same or different. Other preferred heteroaryl groups, optionally substituted, include pyrazinyl, pyrimidinyl, pyridazinyl, furyl, oxadiazolyl, oxazolyl, imidazolyl, 1,3-thiazolyl, thiadiazolyl and pyrazolyl.

As used herein, the term $C_1$-$C_6$ haloalkyl is an alkyl group as defined above, attached to 1, 2 or 3 halogen atoms, such as chlorine, fluorine, bromine or iodine. Preferred halogen atoms are chlorine and fluorine.

As used herein, some of the atoms, radicals, chains or cycles present in the general structures of the invention are "optionally substituted". This means that these atoms, radicals, chains or cycles can be either unsubstituted or substituted in any position by one or more, for example 1, 2, 3 or 4 substituents, whereby the hydrogen atoms bound to the unsubstituted atoms, radicals, chains or cycles are substituted by halogen atom, $C_3$-$C_{12}$ cycloalkyl, hydroxy, $C_1$-$C_6$ alcoxy lineal or branched, $C_1$-$C_6$ alkylthio, amino, mono- or dialkylamino, $C_1$-$C_6$ alcoxyalkyl, hydroxycarbonyl and $C_2$-$C_6$ alcoxycarbonyl. When two or more substituents are present, each substituent may be the same or different.

As used herein, the term pharmaceutically acceptable salt encompasses salts with acid or base acceptable pharmaceutically. The pharmaceutically acceptable acids include inorganic acids, for example hydrochloric acid, sulphuric acid, phosphoric acid, diphosphoric acid, hydrobromic acid, hydroiodic acid and nitric acid, and organic acids such as citric, maleic, malic, mandelic, ascorbic, oxalic, succinic, tartaric, acetic, methanesulphonic, ethanesulphonic, benzenesulphonic or p-toluenesulphonic. Pharmaceutically acceptable bases include alkali metal (e.g. sodium or potassium and alkaline earth metals (e.g. calcium or magnesium) hydroxides and organic bases, for example alkylamines, arylalkylamines and heterocyclic amines.

Other preferred salts according to the invention are quaternary ammonium compounds wherein an equivalent of an anion (X–) with the positive charge of the N atom. X– may be an anion of various mineral acids such as chloride, bromide, iodide, sulphate, nitrate, phosphate, or an anion of an organic acid such as acetate, maleate, fumarate, citrate, oxalate, succinate, tartrate, malate, mandelate, trifluoroacetate, methanesulfonate and p-toluenesulfonate. $X^-$ is preferably an anion selected from chloride, bromide, iodide, sulfate, nitrate, acetate, maleate, oxalate, succinate or trifluoroacetate. More preferably $X^-$ is chloride, bromide, trifluoroacetate or methanesulfonate.

According to one embodiment of the present invention in the compounds of formula (I), $R^1$ represents a five or six-membered heteroaryl group optionally substituted by 1, 2 or 3 substituents selected from halogen atom, $C_1$-$C_6$ haloalkyl linear or branched, $C_1$-$C_6$ alkyl linear or branched, $C_1$-$C_6$ alkoxy linear or branched and cyano group. In a preferred embodiment of the present invention $R^1$ represents a group selected from thienyl, furyl, pyridyl and thiazolyl optionally substituted by 1, 2 or 3 substituents selected from the group consisting of halogen atom, $C_1$-$C_6$ alkyl linear or branched, $C_1$-$C_6$ alkoxy linear or branched and cyano group. In a preferred embodiment of the present invention $R^1$ represents a thienyl group optionally substituted by 1, 2 or 3 substituents selected from the group consisting of halogen atom and $C_1$-$C_6$ alkoxy linear or branched.

According to one embodiment of the present invention in the compounds of formula (I), $R^1$ represents a phenyl group optionally substituted by 1, 2 or 3 substituents selected from the group consisting of halogen atom, $C_1$-$C_6$ haloalkyl linear or branched, $C_1$-$C_6$ alkyl linear or branched, $C_1$-$C_6$ alkoxy linear or branched and cyano group. In a preferred embodiment of the present invention $R^1$ represents a phenyl group optionally substituted by 1, 2 or 3 substituents selected from the group consisting of halogen atom and $C_1$-$C_6$ alkoxy linear or branched.

Particular compounds of the invention include:
1-(5-(5-cyano-4-phenylthiazol-2-ylcarbamoyl)pyridin-2-yl)piperidine-4-carboxylic acid
1-(5-((5-cyano-4-(2-methoxyphenyl)thiazol-2-yl)carbamoyl)pyridin-2-yl)piperidine-4-carboxylic acid
1-(5-((5-cyano-4-(3-methoxyphenyl)thiazol-2-yl)carbamoyl)pyridin-2-yl)piperidine-4-carboxylic acid
1-(5-(5-cyano-4-(4-methoxyphenyl)thiazol-2-ylcarbamoyl)pyridin-2-yl)piperidine-4-carboxylic acid
1-(5-((5-cyano-4-(2-fluorophenyl)thiazol-2-yl)carbamoyl)pyridin-2-yl)piperidine-4-carboxylic acid
1-(5-((5-cyano-4-(3-fluorophenyl)thiazol-2-yl)carbamoyl)pyridin-2-yl)piperidine-4-carboxylic acid
1-(5-((5-cyano-4-(4-fluorophenyl)thiazol-2-yl)carbamoyl)pyridin-2-yl)piperidine-4-carboxylic acid
1-(5-((4-(2-chlorophenyl)-5-cyanothiazol-2-yl)carbamoyl)pyridin-2-yl)piperidine-4-carboxylic acid
1-(5-((5-cyano-4-(pyridin-2-yl)thiazol-2-yl)carbamoyl)pyridin-2-yl)piperidine-4-carboxylic acid
1-(5-((5-cyano-4-(pyridin-3-yl)thiazol-2-yl)carbamoyl)pyridin-2-yl)piperidine-4-carboxylic acid
1-(5-(5-cyano-4-(pyridin-4-yl)thiazol-2-ylcarbamoyl)pyridin-2-yl)piperidine-4-carboxylic acid
1-(5-(5-cyano-4-(6-methoxypyridin-3-yl)thiazol-2-ylcarbamoyl)pyridin-2-yl)piperidine-4-carboxylic acid
1-(5-(5-cyano-4-(furan-2-yl)thiazol-2-ylcarbamoyl)pyridin-2-yl)piperidine-4-carboxylic acid
1-(5-(5-cyano-4-(thiophen-2-yl)thiazol-2-ylcarbamoyl)pyridin-2-yl)piperidine-4-carboxylic acid
1-(5-(5-cyano-4-(thiophen-3-yl)thiazol-2-ylcarbamoyl)pyridin-2-yl)piperidine-4-carboxylic acid
1-(5-((4-(4-chlorothiophen-2-yl)-5-cyanothiazol-2-yl)carbamoyl)pyridin-2-yl)piperidine-4-carboxylic acid
1-(5-(5-cyano-4-(thiazol-2-yl)thiazol-2-ylcarbamoyl)pyridin-2-yl)piperidine-4-carboxylic acid Compounds defined by formula (I) of the present invention can be synthesized by using the procedures described below.

Scheme 1

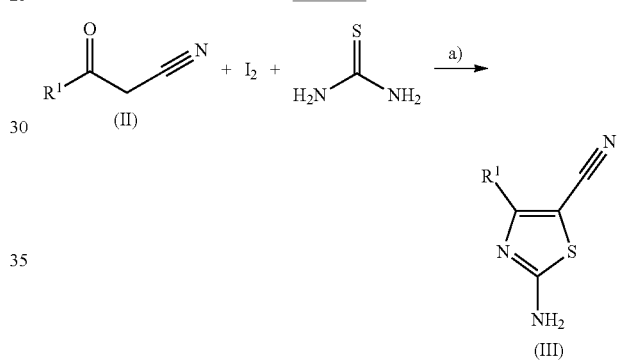

a) pyrdine, 40-100° C., 5-12 h.

2-amino-4-cyano-1,3-thiazoles of formula (III) can be obtained by reacting the commercially available cyanoketones of formula (II) with iodine and thiourea at temperatures between 40° to 100° C. and pyridine as solvent according to shown in scheme 1.

In the case where cyanoketones are non-commercial, they can be synthesized following the reaction shown in Scheme 2.

Scheme 2

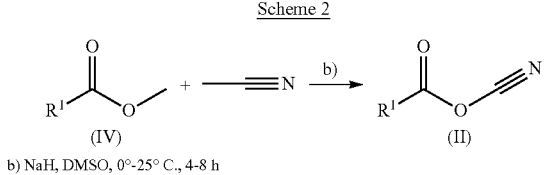

b) NaH, DMSO, 0°-25° C., 4-8 h

Non-commercial cyanoketones (II) can be synthesized from the reaction of the corresponding esters (IV) with acetonitrile in DMSO in the presence of sodium hydride, following methods known in the state of the art. The derivatives of formula (II) obtained are subsequently used without further purification.

Scheme 3

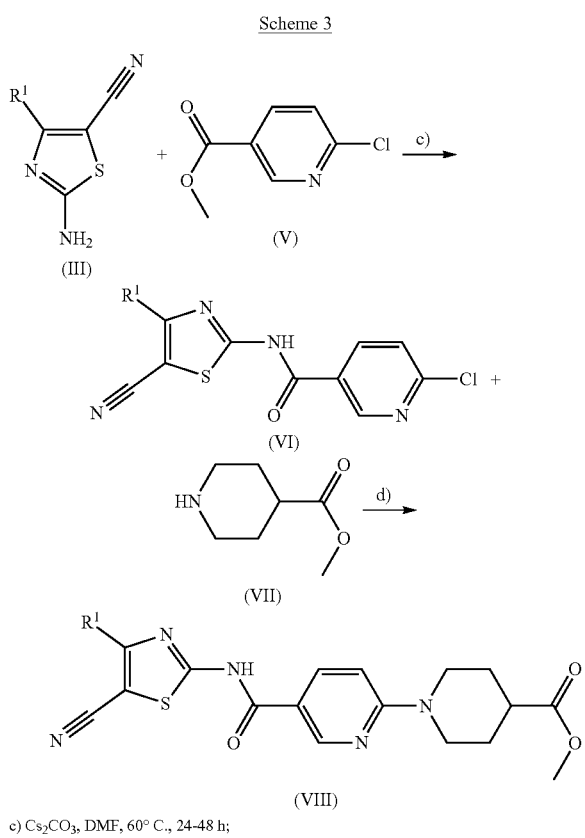

c) Cs₂CO₃, DMF, 60° C., 24-48 h;
d) DMSO, 80° C., 8 h 2-amino-4-cyano-1,3-thiazoles (III) react with the commercial esters of formula (V), to give amides of formula (VI), which in turn are converted into derivatives of formula (VIII) when reacting with the corresponding commercial amines of formula (VII) such as methyl isonipecotate in DMSO at temperatures between 60° and 100° C. in a period of 4 to 12 hours.

Scheme 4

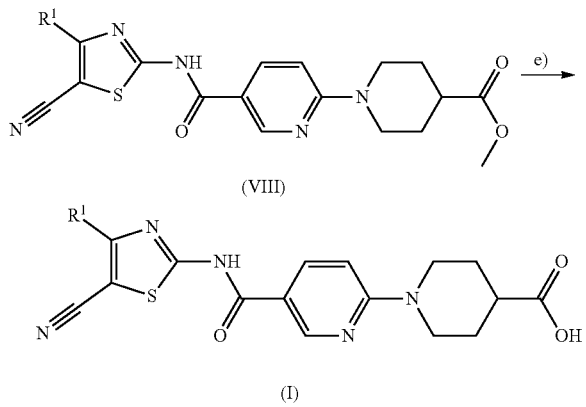

e) THF/NaOH 1M, room tempearture

Finally, the derivatives of formula (VIII) are hydrolyzed in a mixture of THF and sodium hydroxide 1M, at room temperature to obtain acids which correspond to the compounds formula (I) according to the invention.

Pharmacological Activity

Human membranes for recombinant adenosine receptors were purchased from Receptor Biology, Inc. (USA).

$A_3$ Adenosine Receptor Competition Radioligand Binding Assay

Competitive assays were carried out by incubation of membranes from human $A_3$ receptors transfected to CHO cells, [$^3$H]-NECA, buffer (20 mM HEPES (pH 7.4), 100 mM NaCl, 10 mM MgCl₂, 2 units/ml adenosine deaminase), and unlabelled ligand in a total volume of 0.2 ml for 60 min at 25° C. R-PIA was used to determine nonspecific binding. It was filtered over Schleicher & Schuell GF/52 (presoaked with 0.5% polyethyleneimine) in a Brandel cell harvester. The unbound radioligand was removed with 3×250 μl of 20 mM HEPES (pH 7.4), 100 mM NaCl, 10 mM MgCl₂.

$A_{2A}$ Adenosine Receptor Competition Radioligand Binding Assay

Competitive assays were carried out by incubation of membranes from human $A_{2A}$ receptors transfected to HeLa cells, [$^3$H]-ZM241385, buffer (Tris-HCl 50 mM (pH=7.4), 10 mM MgCl₂, EDTA 1 mM and 2 units/ml adenosine deaminase), and unlabelled ligand in a total volume of 0.2 ml for 60 min at 25° C. NECA was used to determine nonspecific binding. It was filtered over Schleicher & Schuell GF/52 (presoaked with 0.5% polyethyleneimine) in a Brandel cell harvester. The unbound radioligand was removed with 3×250 μl of 20 mM Tris-HCl 50 mM (pH=7.4), 10 mM MgCl₂, EDTA 1 mM.

$A_{2B}$ Adenosine Receptor Competition Radioligand Binding Assay

The binding assay for adenosine $A_{2B}$ receptor subtype was carried out on human recombinant source (HEK-293 cells) and [$^3$H]DPCPX as radioligand, according to assay disclosed by Fredholm et al. (International Union of Pharmacology. XXV. Nomenclature and classification of adenosine receptors, Pharmacol Rev. 2001 December; 53(4):527-52).

Adenosine $A_1$ Receptor Subtype Competition Radioligand Binding Assay

Competition assays were carried out by incubation of human recombinant membranes of adenosine receptors (Receptor Biology, Inc.) from hA1 receptors transfected to CHO cells, [$^3$H] DPCPX as radioligand, buffer (HEPES 20 mM (pH=7.4), 10 mM MgCl₂, 100 mM NaCl, 2 U/mL of deaminase adenosine and non-labelled ligand in a total volume of 0.2 mL for 90 min at 25° C. R-PIA was used to determinate non-specific binding. Filter over Schleicher & Schuell GF/52 (pre-soaked 0.5% polyethylenimine) in a Brandel cell harvester. Unbound radioligand was removed with HEPES 30 mM (3×250 μl), NaCl (100 mM) and MgCl₂ (10 mM).

Table 1 shows Ki values in the adenosine receptors of some exemplified compounds.

| Example | Binding to adenosine $A_3$ receptor (Ki - nM) | Binding to adenosine $A_{2A}$ receptor (Ki - nM) | Binding to adenosine $A_{2B}$ receptor (Ki - nM) | Binding to adenosine $A_1$ receptor (Ki - nM) |
|---|---|---|---|---|
| 1 | 103.1 | >1000 | >500 | >500 |
| 3 | 65.5 | >1000 | >1000 | >1000 |
| 4 | 47.6 | >1000 | >1000 | >1000 |
| 5 | 26.3 | >1000 | >500 | >500 |
| 6 | 50.3 | >1000 | >1000 | >1000 |
| 14 | 29.2 | >500 | >1000 | >500 |

From the above results it can be concluded that the compounds of formula (I) claimed in the present invention are potent and selective adenosine $A_3$ receptor modulators.

Another aspect of the present invention is addressed to the use of a compound of formula (I) according to the present invention for the manufacture of a medicament for the treatment of a pathological disease or condition susceptible to improvement by the modulation of $A_3$ adenosine receptors.

Compounds of the present invention are useful in the treatment or prevention of diseases known to be ameliorated by the modulation of $A_3$ adenosine receptors, such as cardiovascular diseases such as atherosclerosis, respiratory diseases such as asthma, cancer diseases such as prostate cancer, kidney diseases such as acute renal failure, autoimmune diseases such as arthritis rheumatoid, diseases of gastrointestinal system such as Crohn's disease, colitis or irritable bowel syndrome or ophthalmological diseases or conditions such as glaucoma, dry eye syndrome or uveitis.

Accordingly, the derivatives of the invention and pharmaceutically acceptable salts thereof, and pharmaceutical compositions comprising such compounds and/or salts thereof, may be used in a method of treatment of disorders of the human body which comprises administering to a subject requiring such treatment an effective amount of 2-amino-1,3-thyazol derivative of formula (I) of the invention or a pharmaceutically acceptable salt thereof.

The present invention also provides pharmaceutical compositions which comprise, as an active ingredient, at least a amidothiazol derivatives of formula (I) or a pharmaceutically acceptable salt thereof in association with, other therapeutics agents a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably, the compositions are made up in a form suitable for oral, topical, nasal, rectal, percutaneous or injectable administration.

The pharmaceutically acceptable excipients which are admixed with the active compound, or salts of such compound, to form compositions of this invention are well known per se and the actual excipients used depend inter alia on the intended method of administering the compositions.

The compositions of this invention are adapted preferably for injectable and per os administration. In this case, the compositions for oral administration may take the form of tablets, prolonged action tablets, sublingual tablets, capsules, inhalation aerosols, inhalation solutions, dry powder inhalation, or liquid preparations, such as mixtures, elixirs, syrups or suspensions, all containing the compound of the invention; such preparations may be prepared by methods known in the art.

The diluents which may be used in the preparation of the compositions include those liquid and solid diluents which are compatible with the active ingredient, together with coloring or flavoring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound together with, for example, sucrose to form a syrup. The suspensions may comprise an insoluble active compound of the invention or a pharmaceutically acceptable salt thereof together with water and with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

Another aspect of the invention is addressed to a combination product comprising a compound of formula (I) according to has been defined previously and other drugs accepted to treat diseases of central nervous system as for example Alzheimer's disease, cardiovascular disease as for example atherosclerosis, respiratory diseases as asthma, renal disease as acute renal failure, oncologic diseases as prostate cancer, autoimmune diseases as rheumatoid arthritis or diseases of the gastrointestinal system such as irritable bowel syndrome.

Another aspect of the invention is addressed to a combination product comprising a compound of formula (I) according to has been defined previously, and other drugs, wherein the other drugs are selected from the group consisting of inhibitors of 3-hydroxy-3-methyl-glutaryl-CoA reductase (HMG-CoA reductase) also known as statins including atorvastatin, rosuvastatin and simvastatin, leukotriene receptor antagonists such as Montelukast, gonadotropin releasing hormone (GnRH) agonist such as Bicalutamide, antiandrogen drugs such as Flutamide, inhibitors of Janus-kinase 1 and 3 (JAK 1 and 3) enzymes such as Tofacitinib, diuretic agents such as Hydrochlorothiazide and activators of secretion of intestinal fluids such as Lubiprostone.

The present invention will be further illustrated by the following examples and they do not limit the scope of the invention in any way.

EXAMPLES

The synthesis of compounds and intermediates of the invention for use herein are illustrated by the following Examples (1 to 52), including the preparation of the intermediates, which do not limit in any way the scope of the present invention.

General.

Reagents, solvents and starting materials were purchased from commercial suppliers. Concentration refers to evaporation under vacuum using a Büchi rotatory evaporator. Reaction products were purified when necessary, by flash chromatography on silica gel (40-63 µm) with the solvent system indicated. Spectroscopic data were recorded on a Varian Gemeni 300 spectrometer. Melting points were recorded on a Büchi 535 apparatus. HPLC-MS were performed on a Gilson instrument equipped with a Gilson piston pump 321, a Gilson 864 vacuum degasser, a Gilson 189 injection module, a 1/1000 splitter, a Gilson 307 make-up pump, a Gilson 170 diode array detector, and a Thermoquest Fennigan aQa detector.

Intermediate 1:
3-(4-chlorothiophen-2-yl)-3-oxo-propanenitrile

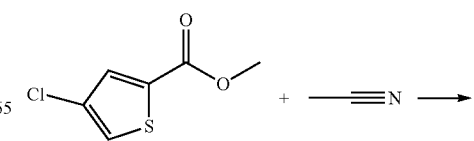

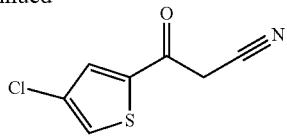

To a solution of 0.5 g (2.83 mmol) of methyl 4-chlorothiophene-2-carboxylate in 1.2 ml of DMSO in 25 ml flask is added 0.22 ml (4.24 mmol) of acetonitrile. The mixture is stirred at 0° C. and 0.147 g (3.68 mmol) of NaH (60% in mineral oil) is added. The reaction is stirred at room temperature under nitrogen for 8 h. This intermediate was used in the next step without further purification (one pot reaction).

The following intermediate was synthesized using the procedure described for Intermediate 1 using the corresponding esters.

Intermediate 2: 3-oxo-3-(thiazol-2-yl) Propanenitrile

The intermediate was used in the following step without further purification (one pot reaction).

Intermediate 3: 2-amino-4-(2-fluorophenyl) thiazole-5-carbonitrile

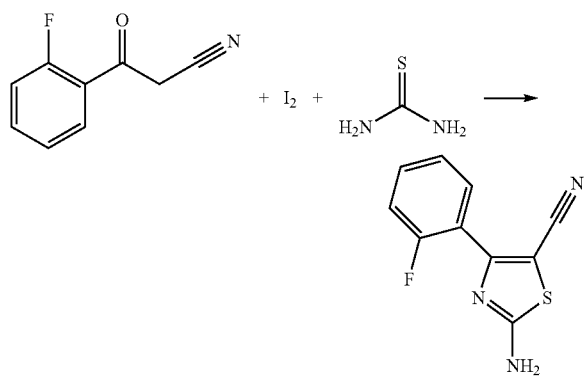

1.0 g (6.13 mmol) of 3-(2-fluorophenyl)-3-oxopropanonitrile are dissolved in 5 ml of pyridine and 0.61 g (7.97 mmol) of thiourea and 1.56 g (6.13 mmol) of iodine are added. The solution is heated for 6 hours at 90° C. It is then allowed to cool to room temperature and poured into 50 ml of ice water. The resulting precipitate is filtered, washed several times with water and 1.12 g (83.15%) of a light brown solid is obtained.

$^1$H-NMR (400 MHz, DMSO-$d_6$): δ=8.26 (s, 2H), 7.64 (m, 1H), 7.54 (d, 1H), 7.32 (m, 2H).
HPLC-MS: Rt 2.950, m/z 219.4 (MH$^+$).

The following intermediates were synthesized using the procedure described for Intermediate 3 from the corresponding acetonitrile.

Intermediate 4: 2-amino-4-(3-fluorophenyl) thiazole-5-carbonitrile $^1$H-NMR (400 MHz, DMSO-$d_6$): δ=8.28 (s, 2H), 7.77 (m, 1H), 7.64 (ddd, 1H), 7.57 (m, 1H), 7.34 (td, 1H).
HPLC-MS: Rt 3.373, m/z 220.0 (MH$^+$).

Intermediate 5: 2-amino-4-(4-fluorophenyl) thiazole-5-carbonitrile $^1$H-NMR (400 MHz, DMSO-$d_6$): δ=8.25 (s, 2H), 7.97 (dd, 2H), 7.36 (t, 2H).
HPLC-MS: Rt 3.316, m/z 220.0 (MH$^+$).

Intermediate 6: 2-amino-4-phenylthiazole-5-carbonitrile $^1$H-NMR (400 MHz, DMSO-$d_6$): δ=8.39 (d, 2H), 8.09 (d, 2H) 7.55 (t, 2H), 7.47 (t, 1H).
HPLC-MS: Rt 3.351 m/z 202.0 (MH$^+$).

Intermediate 7: 2-amino-4-(2-methoxyphenyl) thiazole-5-carbonitrile $^1$H-NMR (400 MHz, DMSO-$d_6$): δ=8.12 (s, 2H), 7.44 (t, 2H), 7.15 (d, 1H), 7.02 (t, 1H), 3.82 (s, 3H).
HPLC-MS: Rt 3.199, m/z 332.0 (MH$^+$).

Intermediate 8: 2-amino-4-(3-methoxyphenyl) thiazole-5-carbonitrile $^1$H-NMR (400 MHz, DMSO-$d_6$): δ=8.26 (s, 2H), 7.51 (ddd, 1H), 7.45 (dd, 1H), 7.42 (d, 1H), 7.06 (ddd, 1H), 3.80 (s, 3H).
HPLC-MS: Rt 3.530, m/z 232.0 (MH$^+$).

Intermediate 9: 2-amino-4-(4-methoxyphenyl) thiazole-5-carbonitrile $^1$H-NMR (400 MHz, DMSO-$d_6$): δ=8.38 (d, 2H), 8.08 (d, 2H) 7.09 (d, 2H), 3.84 (s, 3H).
HPLC-MS: Rt 3.894, m/z 231.9 (MH$^+$).

Intermediate 10: 2-amino-4-(2-chlorophenyl) thiazole-5-carbonitrile $^1$H-NMR (400 MHz, DMSO-$d_6$): δ=8.27 (s, 1H), 7.60 (dd, 1H), 7.52 (m, 2H), 7.45 (td, 1H).
HPLC-MS: Rt 3.798, m/z 235.9 (MH$^+$).

Intermediate 11: 2-amino-4-(pyridin-2-yl) thiazole-5-carbonitrile $^1$H-NMR (400 MHz, DMSO-$d_6$): δ=8.66 (d, 1H), 8.21 (s, 2H), 7.93 (m, 2H), 7.46 (m, 1H).
HPLC-MS: Rt 2.909 m/z 203.0 (MH$^+$).

Intermediate 12: 2-amino-4-(pyridin-3-yl) thiazole-5-carbonitrile $^1$H-NMR (400 MHz, DMSO-$d_6$): δ=9.07 (d, 1H), 8.67 (dd, 1H), 8.33 (s, 2H), 8.25 (d, 1H), 7.56 (dd, 1H).
HPLC-MS: Rt 2.249, m/z 203.0 (MH$^+$).

Intermediate 13: 2-amino-4-(pyridin-4-yl) thiazole-5-carbonitrile $^1$H-NMR (400 MHz, DMSO-$d_6$): δ=8.74 (d, 2H), 8.35 (s, 2H), 7.83 (d, 2H).
HPLC-MS: Rt 2.224 m/z 203.0 (MH$^+$).

Intermediate 14: 2-amino-4-(6-methoxypyridin-3-yl) thiazole-5-carbonitrile $^1$H-NMR (400 MHz, DMSO-$d_6$): δ=8.71 (d, 1H), 8.27 (s, 2H) 8.17 (dd, 1H), 6.97 (d, 1H), 3.91 (s, 3H).
HPLC-MS: Rt 2.949, m/z 233.0 (MH$^+$).

Intermediate 15: 2-amino-4-(furan-2-yl)thiazole-5-carbonitrile $^1$H-NMR (400 MHz, DMSO-d$_6$): δ=8.22 (s, 2H), 7.89 (d, 1H), 6.93 (d, 1H), 6.68 (dd, 1H).
HPLC-MS: Rt 2.615, m/z 192.0 (MH$^+$).

Intermediate 16: 2-amino-4-(thiophen-2-yl)thiazole-5-carbonitrile $^1$H-NMR (400 MHz, DMSO-d$_6$): δ=8.29 (s, 2H), 7.78 (d, 1H), 7.74 (d, 1H), 7.21 (dd, 1H).
HPLC-MS: Rt 3.141, m/z 208.0 (MH$^+$).

Intermediate 17: 2-amino-4-(thiophen-3-yl)thiazole-5-carbonitrile $^1$H-NMR (400 MHz, DMSO-d$_6$): δ=8.21 (s, 2H), 8.06 (dd, 1H), 7.70 (dd, 1H), 7.63 (dd, 1H).
HPLC-MS: Rt 3.320, m/z 208.0 (MH$^+$).

Intermediate 18: 2-amino-4-(4-chlorothiophen-2-yl)thiazole-5-carbonitrile $^1$H-NMR (400 MHz, DMSO-d$_6$): δ=8.36 (s, 2H), 7.79 (d, 1H), 7.63 (d, 1H).
HPLC-MS: Rt 3.639, m/z 241.9 (MH$^+$).

Intermediate 19: 2-amino-4-(thiazol-2-yl)thiazole-5-carbonitrile $^1$H-NMR (400 MHz, DMSO-d$_6$): δ=8.39 (s, 2H), 8.04 (d, 1H), 7.94 (d, 1H).
HPLC-MS: Rt 2.528, m/z 209.0 (MH$^+$).

Intermediate 20: 6-chloro-N-(5-cyano-4-phenylthiazol-2-yl)nicotinamide

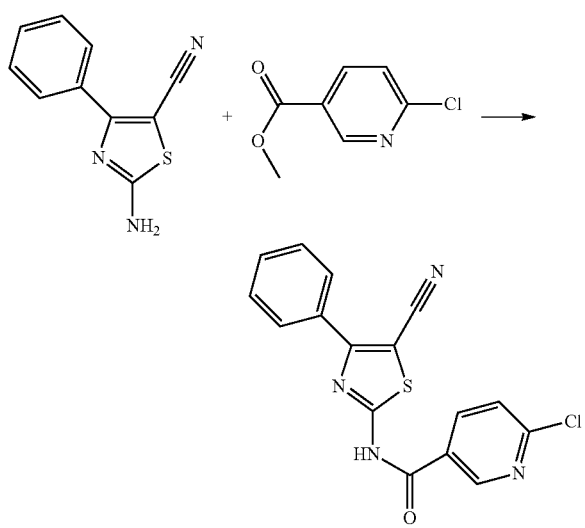

A solution of 0.300 g (1.50 mmol) of 2-amino-4-phenylthiazole-5-carbonitrile, 0.281 g (0.64 mmol) of methyl 6-chloronicotinate and 0.583 g (1.79 mmol) of cesium carbonate in 0.8 mL of DMF is stirred at 60° C. for two days. Then, the reaction mixture is poured into cold water, the precipitate forming is filtered under vacuum. The solid obtained is washed twice with water and dried to obtain 0.485 g (95.50%) of the desired nicotinamide derivative.

$^1$H-NMR (400 MHz, DMSO-d$_6$): δ=13.84 (s, 1H), 9.10 (d, J=2.5 Hz, 1H), 8.50 (dd, J=8.4, 2.6 Hz, 1H), 8.04 (dd, J=8.2, 1.4 Hz, 2H), 7.76 (d, J=8.4 Hz, 1H), 7.58 (m, 3H).
HPLC-MS: Rt 3.173, m/z 341.0 (MH$^+$).

The following intermediates were synthesized using the procedure described for Intermediate 20 from the corresponding 2-aminothiazoles.

Intermediate 21: 6-chloro-N-(5-cyano-4-(2-fluorophenyl)thiazol-2-yl)nicotinamide $^1$H-NMR (400 MHz, DMSO-d$_6$): δ=13.92 (s, 1H), 9.09 (d, 1H), 8.50 (dd, 1H), 7.76 (m, 2H), 7.62 (m, 1H), 7.44 (m, 2H).
HPLC-MS: Rt 3.297, m/z 359.0 (MH$^+$).

Intermediate 22: 6-chloro-N-(5-cyano-4-(3-fluorophenyl)thiazol-2-yl)nicotinamide $^1$H-NMR (400 MHz, DMSO-d$_6$): δ=13.90 (s, 1H), 9.10 (d, 1H), 8.50 (dd, 1H), 7.90 (m, 1H), 7.79 (m, 2H), 7.66 (m, 1H), 7.43 (td, 1H).
HPLC-MS: Rt 3.536, m/z 359.0 (MH$^+$).

Intermediate 23: 6-chloro-N-(5-cyano-4-(4-fluorophenyl)thiazol-2-yl)nicotinamide $^1$H-NMR (400 MHz, DMSO-d$_6$): δ=9.07 (d, 1H), 8.46 (dd, 1H), 8.08 (dd, 2H), 7.63 (d, 1H), 7.39 (t, 3H).
HPLC-MS: Rt 3.495, m/z 359.0 (MH$^+$).

Intermediate 24: 6-chloro-N-(4-(2-chlorophenyl)-5-cyanothiazol-2-yl)nicotinamide $^1$H-NMR (400 MHz, DMSO-d$_6$): δ=9.07 (d, 1H), 8.47 (dd, 1H), 7.60 (m, 6H).
HPLC-MS: Rt 3.409, m/z 374.9 (MH$^+$).

Intermediate 25: 6-chloro-N-(5-cyano-4-(2-methoxyphenyl)thiazol-2-yl)nicotinamide $^1$H-NMR (400 MHz, DMSO-d$_6$): δ=13.83 (s, 1H), 9.10 (s, 1H), 8.50 (d, 1H), 7.76 (d, 1H), 7.64 (m, 2H), 7.23 (d, 1H), 7.11 (t, 1H), 3.86 (s, 3H).
HPLC-MS: Rt 3.193, m/z 371.0 (MH$^+$).

Intermediate 26: 6-chloro-N-(5-cyano-4-(3-methoxyphenyl)thiazol-2-yl)nicotinamide $^1$H-NMR (400 MHz, DMSO-d$_6$): δ=13.81 (s, 1H), 9.09 (dd, 1H), 8.48 (dd, 1H), 7.70 (d, 1H), 7.63 (dd, 1H), 7.63 (m, 1H), 7.48 (t, 1H), 7.09 (dd, 1H), 3.83 (s, 3H).
HPLC-MS: Rt 3.488, m/z 371.0 (MH$^+$).

Intermediate 27: 6-chloro-N-(5-cyano-4-(4-methoxyphenyl)thiazol-2-yl)pyridine-3-carboxamide $^1$H-NMR (400 MHz, DMSO-d$_6$): δ=13.76 (s, 1H), 9.08 (s, 1H), 8.48 (d, 1H), 8.01 (d, 2H), 7.73 (d, 1H), 7.13 (d, 2H), 3.84 (s, 3H).
HPLC-MS: Rt 3.481, m/z 371.0 (MH$^+$).

Intermediate 28: 6-chloro-N-(5-cyano-4-(pyridin-2-yl)thiazol-2-yl)pyridine-3-carboxamide $^1$H-NMR (400 MHz, DMSO-d$_6$): δ=13.86 (s, 1H), 9.10 (d, 1H), 8.75 (m, 1H), 8.50 (dd, 1H), 8.09 (d, 1H), 8.03 (td, 1H), 7.77 (d, 1H), 7.54 (ddd, 1H).
HPLC-MS: Rt 2.990, m/z 342.0 (MH$^+$).

Intermediate 29: 6-chloro-N-(5-cyano-4-(pyridin-3-yl)thiazol-2-yl)pyridine-3-carboxamide $^1$H-NMR (400 MHz, DMSO-d$_6$): δ=13.91 (s, 1H), 9.19 (d, 1H), 9.10 (d, 1H), 8.73 (dd, 1H), 8.50 (dd, 1H), 8.36 (m, 1H), 7.77 (d, 1H), 7.64 (dd, 1H).
HPLC-MS: Rt 2.963, m/z 341.9 (MH$^+$).

Intermediate 30: 6-chloro-N-(5-cyano-4-(pyridin-4-yl)thiazol-2-yl)pyridine-3-carboxamide $^1$H-NMR (400 MHz, DMSO-d$_6$): δ=13.91 (s, 1H), 9.10 (d, 1H), 8.82 (d, 2H), 8.50 (dd, 1H), 7.95 (d, 2H), 7.76 (d, 1H).
HPLC-MS: Rt 2.890, m/z 342.0 (MH$^+$).

Intermediate 31: 6-chloro-N-(5-cyano-4-(6-methoxypyridin-3-yl)thiazol-2-yl)pyridine-3-carboxamide $^1$H-NMR (400 MHz, DMSO-d$_6$): δ=9.07 (d, 1H), 8.82 (d, 1H), 8.46 (dd, 1H), 8.29 (dd, 1H), 7.60 (d, 1H), 6.99 (d, 1H), 3.93 (s, 3H).
HPLC-MS: Rt 2.970, m/z 372.0 (MH$^+$).

Intermediate 32: 6-chloro-N-(5-cyano-4-(furan-2-yl)thiazol-2-yl)pyridine-3-carboxamide $^1$H-NMR (400 MHz, DMSO-d$_6$): δ=12.87 (s, 1H), 9.06 (d, 1H), 8.44 (d, 1H), 7.87 (s, 1H), 7.59 (d, 1H), 7.00 (d, 1H), 6.68 (dd, 1H).
HPLC-MS: Rt 2.834, m/z 331.0 (MH$^+$).

Intermediate 33: 6-chloro-N-(5-cyano-4-(thiophen-2-yl)thiazol-2-yl)pyridine-3-carboxamide $^1$H-NMR (400 MHz, DMSO-d$_6$): δ=13.85 (s, 1H), 9.09 (d, 1H), 8.49 (dd, 1H), 7.91 (dd, 1H), 7.84 (dd, 1H), 7.76 (d, 1H), 7.28 (dd, 1H).
HPLC-MS: Rt 3.123, m/z 347.0 (MH$^+$).

Intermediate 34: 6-chloro-N-(5-cyano-4-(thiophen-3-yl)thiazol-2-yl)pyridine-3-carboxamide $^1$H-NMR (400 MHz, DMSO-d$_6$): δ=9.05 (dd, 1H), 8.44 (ddd, 1H), 8.11 (dd, 1H), 7.75 (dt, 1H), 7.68 (ddd, 1H), 7.56 (dd, 1H).
HPLC-MS: Rt 3.348, m/z 347.0 (MH$^+$).

Intermediate 35: 6-chloro-N-(4-(4-chlorothiophen-2-yl)5-cyanothiazol-2-yl)pyridine-3-carboxamide $^1$H-NMR (400 MHz, DMSO-d$_6$): δ=9.06 (d, 1H), 8.44 (dd, 1H), 7.74 (d, 1H), 7.66 (d, 1H), 7.58 (d, 1H).
HPLC-MS: Rt 3.822, m/z 380.9 (MH$^+$).

Intermediate 36: 6-chloro-N-(5-cyano-4-(thiazol-2-yl)thiazol-2-yl)pyridine-3-carboxamide $^1$H-NMR (400 MHz, DMSO-d$_6$): δ=9.07 (d, 1H), 8.45 (dd, 1H), 8.00 (d, 1H), 7.87 (d, 1H), 7.57 (d, 1H).
HPLC-MS: Rt 2.939, m/z 348.0 (MH$^+$).

Intermediate 37: methyl 1-(5-(5-cyano-(4-phenylthiazol-2-ylcarbamoyl)pyridin-2-yl)piperidine-4-carboxylate

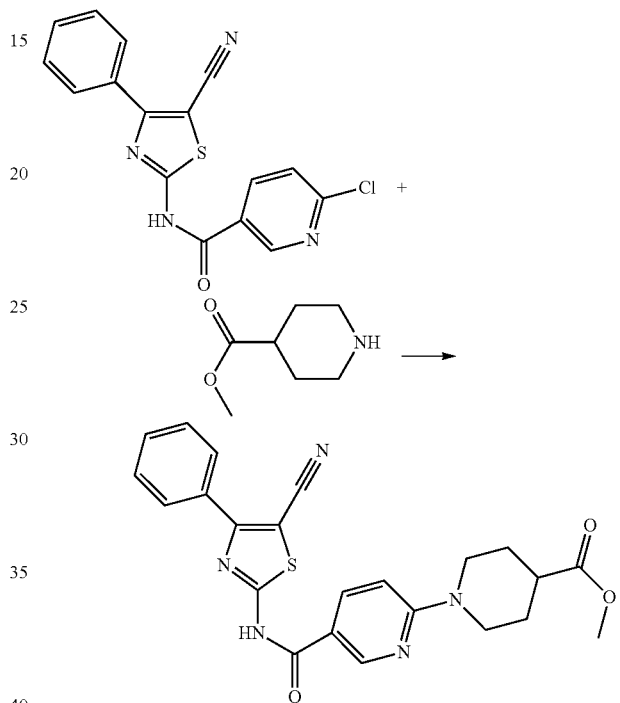

To a solution of 0.512 g (1.5 mmol) of 6-chloro-N-(5-cyano-4-phenylthiazol-2-yl)nicotinamide in 1 mL of DMSO is added 1.01 mL (7.5 mmol) of methyl piperidine-4-carboxylate and stirred at 90° C. for 12 hours. The reaction mixture is poured into a cold saturated solution of sodium hydrogencarbonate. The formed precipitate is filtered, washed with water several times and purified by normal phase chromatography. 0.454 g (67.48%) are obtained.

$^1$H-NMR (400 MHz, DMSO-d$_6$): δ=8.86 (s, 1H), 8.19 (dd, 1H), 8.03 (d, 1H), 7.51 (m, 1H), 6.88 (d, 1H), 4.33 (d, 1H), 3.62 (s, 2H), 3.06 (t, 1H), 1.91 (d, 1H), 1.55 (dd, 1H).
HPLC-MS: Rt 4.507, m/z 448.1 (MH$^+$).

The following intermediates were synthesized using the procedure described for Intermediate 37 from the corresponding nicotinamide and methyl piperidin-4-carboxylate.

Intermediate 38: methyl 1-(5-((5-cyano-4-(2-methoxyphenyl)thiazol-2-yl)carbamoyl)pyridin-2-yl)piperidine-4-carboxylate $^1$H-NMR (400 MHz, DMSO-d$_6$): δ=13.25 (s, 1H), 8.89 (d, 1H), 8.20 (dd, 1H), 7.57 (dd, 1H), 7.51 (m, 1H), 7.21 (d, 1H), 7.09 (t, 1H), 6.95 (d, 1H), 4.37 (d, 2H), 3.86 (s, 3H), 3.62 (s, 3H), 3.12 (t, 2H), 2.71 (m, 1H), 1.91 (d, 2H), 1.53 (td, 1H).
HPLC-MS: Rt 4.410, m/z 378.1 (MH$^+$).

Intermediate 39: methyl 1-(5-((5-cyano-4-(3-methoxyphenyl)thiazol-2-yl)carbamoyl)pyridin-2-yl)piperidine-4-carboxylate ¹H-NMR (400 MHz, DMSO-d₆): δ=13.27 (s, 1H), 8.89 (d, 1H), 8.21 (dd, 1H), 7.62 (d, 1H), 7.57 (m, 1H), 7.50 (t, 1H), 7.12 (m, 1H), 6.96 (d, 1H), 4.37 (d, 2H), 3.83 (s, 3H), 3.62 (s, 3H), 3.12 (m, 2H), 2.71 (m, 1H), 1.92 (m, 2H), 1.54 (m, 2H).
HPLC-MS: Rt 4.678, m/z 478.1 (MH⁺).

Intermediate 40: methyl 1-(5-(5-cyano-4-(4-methoxyphenyl)thiazol-2-ylcarbamoyl)pyridin-2-yl)piperidine-4-carboxylate ¹H-NMR (400 MHz, DMSO-d₆): δ=13.24 (s, 1H), 8.88 (d, 1H), 8.20 (dd, 1H), 8.01 (d, 2H), 7.14 (d, 2H), 6.95 (d, 1H), 4.37 (d, 2H), 3.84 (s, 3H), 3.62 (s, 3H), 3.12 (t, 2H), 2.71 (m, 1H), 1.91 (d, 2H), 1.53 (dd, 2H).
HPLC-MS: Rt 4.739, m/z 478.1 (MH⁺).

Intermediate 41: methyl 1-(5-((5-cyano-4-(2-fluorophenyl)thiazol-2-yl)carbamoyl)pyridin-2-yl) piperidine-4-carboxylate ¹H-NMR (400 MHz, DMSO-d₆): δ=13.35 (s, 1H), 8.89 (d, 1H), 8.27 (s, 1H), 8.20 (dd, 1H), 7.76 (td, 1H), 7.58 (m, 2H), 7.40 (m, 3H), 6.96 (d, 1H), 4.37 (d, J=13.3 Hz, 2H), 3.61 (s, 3H), 3.12 (m, 2H), 2.71 (m, 1H), 1.91 (dd, 2H), 1.53 (m, 2H).
HPLC-MS: Rt 4.419, m/z 466.1 (MH⁺).

Intermediate 42: methyl 1-(5-((5-cyano-4-(3-fluorophenyl)thiazol-2-yl)carbamoyl)pyridin-2-yl) piperidine-4-carboxylate ¹H-NMR (400 MHz, DMSO-d₆): δ=13.31 (s, 1H), 8.88 (d, 1H), 8.20 (dd, 1H), 7.89 (dd, 1H), 7.77 (m, 1H), 7.65 (m, 1H), 7.41 (td, 1H), 6.95, (d, 1H), 4.37 (d, 2H), 3.61 (s, 3H), 3.12 (m, 2H), 2.71 (m, 1H), 1.91 (dd, 2H), 1.53 (m, 2H).
HPLC-MS: Rt 4.710, m/z 466.1 (MH⁺).

Intermediate 43: methyl 1-(5-((5-cyano-4-(4-fluorophenyl)thiazol-2-yl)carbamoyl)pyridin-2-yl) piperidine-4-carboxylate ¹H-NMR (400 MHz, DMSO-d₆): δ=13.29 (s, 1H), 8.89 (d, 1H), 8.20 (dd, 1H), 8.08 (m, 2H), 7.44 (t, 2H), 6.96 (d, 1H), 4.38 (d, 2H), 3.62 (s, 3H), 3.11 (m, 2H), 2.72 (m, 1H), 1.92 (d, 2H), 1.54 (m, 2H).
HPLC-MS: Rt 4.734, m/z 466.1 (MH⁺).

Intermediate 44: methyl 1-(5-((4-(2-chlorophenyl)-5-cyanothiazol-2-yl)carbamoyl)pyridin-2-yl) piperidine-4-carboxylate ¹H-NMR (400 MHz, DMSO-d₆): δ=13.33 (s, 1H), 8.88 (d, 1H), 8.20 (dd, 1H), 7.59 (d, 4H), 6.96 (d, 1H), 4.37 (d, 2H), 3.62 (s, 3H), 3.12 (m, 2H), 2.69 (d, 1H), 1.91 (dd, 2H), 1.53 (td, 2H).
HPLC-MS: Rt 4.818 m/z 481.9 (MH⁺).

Intermediate 45: methyl 1-(5-((5-cyano-4-(pyridin-2-yl)thiazol-2-yl)carbamoyl)pyridin-2-yl) piperidine-4-carboxylate ¹H-NMR (400 MHz, DMSO-d₆): δ=13.17 (s, 1H), 8.89 (d, 1H), 8.72 (s, 1H), 8.20 (dd, 1H), 8.10 (d, 1H), 8.01 (t, 1H), 7.51 (m, 1H), 6.95 (d, 1H), 4.37 (d, 2H), 3.62 (s, 3H), 3.11 (t, 2H), 2.71 (m, 1H), 1.91 (d, 2H), 1.54 (dd, 2H).
HPLC-MS: Rt 3.924, m/z 449.1 (MH⁺).

Intermediate 46: methyl 1-(5-((5-cyano-4-(pyridin-3-yl)thiazol-2-yl)carbamoyl)pyridin-2-yl) piperidine-4-carboxylate ¹H-NMR (400 MHz, DMSO-d₆): δ=13.36 (s, 1H), 9.18 (s, 1H), 8.88 (s, 1H), 8.72 (d, 1H), 8.35 (d, 1H), 8.20 (d, 1H), 7.63 (dd, 1H), 6.95 (d, 1H), 4.37 (d, 2H), 3.62 (s, 3H), 3.12 (t, 2H), 2.71 (m, 1H), 1.91 (d, 2H), 1.53 (dd, 2H).
HPLC-MS: Rt 3.682, m/z 449.1 (MH⁺).

Intermediate 47: methyl 1-(5-(5-cyano-4-(pyridin-4-yl)thiazol-2-ylcarbamoyl)pyridin-2-yl) piperidine-4-carboxylate ¹H-NMR (400 MHz, DMSO-d₆): δ=13.34 (s, 1H), 8.88 (d, 1H), 8.80 (d, 2H), 8.20 (dd, 1H), 7.95 (d, 2H), 6.94 (d, 1H), 4.37 (d, 2H), 3.62 (s, 3H), 3.10 (t, 2H), 2.71 (m, 1H), 1.91 (d, 2H), 1.53 (dd, 2H).
HPLC-MS: Rt 3.616, m/z 449.1 (MH⁺).

Intermediate 48: methyl 1-(5-(5-cyano-4-(6-methoxypyridin-3-yl)thiazol-2-ylcarbamoyl)pyridin-2-yl) piperidine-4-carboxylate ¹H-NMR (400 MHz, DMSO-d₆): δ=8.87 (d, 1H), 8.82 (d, 1H), 8.28 (dd, 1H), 8.19 (dd, 1H), 7.03 (d, 1H), 6.93 (d, 1H), 4.36 (d, 2H), 3.94 (s, 3H), 3.62 (s, 3H), 3.10 (t, 2H), 2.70 (m, 1H), 1.91 (d, 2H), 1.54 (dd, 2H).
HPLC-MS: Rt 4.033, m/z 479.0 (MH⁺).

Intermediate 49: methyl 1-(5-(5-cyano-4-(furan-2-yl)thiazol-2-ylcarbamoyl)pyridin-2-yl) piperidine-4-carboxylate ¹H-NMR (400 MHz, DMSO-d₆): δ=8.85 (d, 1H), 8.16 (dd, 1H), 7.86 (d, 1H), 7.01 (d, 1H), 6.88 (dd, 1H), 6.70 (d, 1H), 4.33 (d, 2H), 3.62 (s, 3H), 3.07 (t, 2H), 2.67 (m, 1H), 1.89 (d, 2H), 1.54 (dd, 2H).
HPLC-MS: Rt 3.520, m/z 438.1 (MH⁺).

Intermediate 50: methyl 1-(5-(5-cyano-4-(thiophen-2-yl)thiazol-2-ylcarbamoyl)pyridin-2-yl) piperidine-4-carboxylate ¹H-NMR (400 MHz, DMSO-d₆): δ=13.27 (s, 1H), 8.87 (d, 1H), 8.19 (dd, 1H), 7.90 (dd, 1H), 7.81 (dd, 1H), 7.27 (dd, 1H), 6.94 (d, 1H), 4.37 (d, 2H), 3.61 (s, 3H), 3.11 (t, 2H), 2.71 (m, 1H), 1.91 (d, 2H), 1.53 (dd, 2H).
HPLC-MS: Rt 4.828 m/z 453.9 (MH⁺).

Intermediate 51: methyl 1-(5-((5-cyano-4-(thiophen-3-yl)thiazol-2-yl)carbamoyl)pyridin-2-yl) piperidine-4-carboxylate ¹H-NMR (400 MHz, DMSO-d₆): δ=13.29 (s, 1H), 8.89 (d, 1H), 8.24-8.16 (m, 2H), 7.76 (m, 2H), 6.96 (d, 1H), 4.38 (d, 2H), 3.62 (s, 3H), 3.12 (m, 2H), 2.71 (dtd, 1H), 1.91 (dd, 2H), 1.54 (m, 2H).
HPLC-MS: Rt 4.548, m/z 454.1 (MH⁺).

Intermediate 52: methyl 1-(5-(4-(4-chlorothiophen-2-yl)-5-cyanothiazol-2-ylcarbamoyl)pyridin-2-yl) piperidine-4-carboxylate $^1$H-NMR (400 MHz, DMSO-d$_6$): δ=13.28 (s, 1H), 8.87 (d, 1H), 8.19 (dd, 1H), 7.86 (d, 1H), 7.73 (d, 1H), 6.94 (d, 1H), 4.36 (d, 2H), 3.62 (s, 3H), 3.12 (t, 2H), 2.71 (m, 1H), 1.92 (d, 2H), 154 (dd, 2H).

HPLC-MS: Rt 4.746, m/z 488.0 (MH$^+$).

Intermediate 53: methyl 1-(5-(5-cyano-4-(thiazol-2-yl)thiazol-2-ylcarbamoyl)pyridin-2-yl) piperidine-4-carboxylate $^1$H-NMR (400 MHz, DMSO-d$_6$): δ=8.86 (d, 1H), 8.19 (dd, 1H), 8.05 (d, 1H), 7.93 (d, 1H), 6.89 (d, 1H), 4.34 (d, 2H), 3.62 (s, 3H), 3.08 (t, 2H), 2.69 (m, 1H), 1.91 (d, 2H), 1.55 (dd, 2H).

HPLC-MS: Rt 3.764, m/z 355.1 (MH$^+$).

EXAMPLES

Example 1: 1-(5-(5-cyano-4-phenylthiazol-2-ylcarbamoyl)pyridin-2-yl) piperidine-4-carboxylic Acid

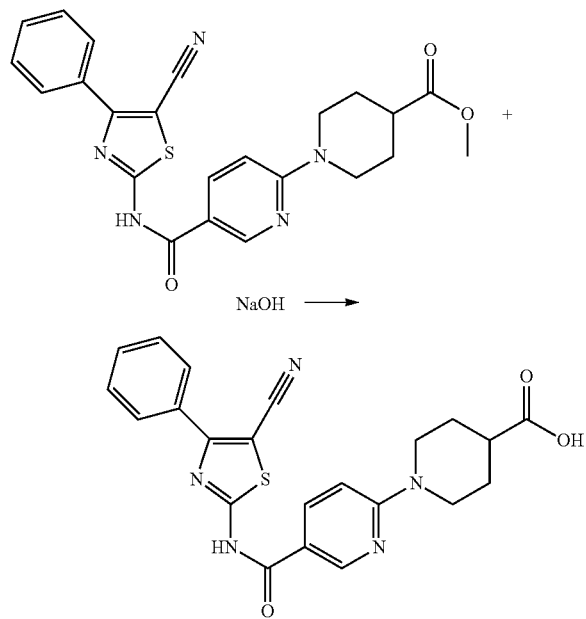

0.08 g (0.178 mmol) of methyl 1-(5-(4-phenylthiazol-2-ylcarbamoyl-5-cyano) pyridin-2-yl) piperidine-4-carboxylate is dissolved in 1.2 mL of THF. To the solution, 0.9 mL (0.9 mmol) of 1M NaOH is added. The reaction mixture is allowed to stir at room temperature until the reaction is completed. Subsequently, it is diluted with 0.1 M NaOH (8 mL) and washed with dichloromethane (3×10 mL). The aqueous phase is acidified with 4 M HCl to pH 3-5, obtaining a light brown precipitated, which is filtered and washed with cold water and subsequently with pentane, obtaining the desired product 0.066 g (85%).

$^1$H-NMR (400 MHz, DMSO-d$_6$): δ=13.28 (s, 1H), 12.28 (s, 1H), 8.89 (s, 1H), 8.21 (d, 1H), 8.03 (d, 2H), 7.58 (dd, 3H), 6.95 (d, 1H), 4.36 (d, 1H), 3.12 (t, 1H), 1.91 (d, 1H), 1.52 (dd, 1H).

HPLC-MS: Rt 2.830, m/z 434.0 (MH$^+$).

Example 2: 1-(5-((5-cyano-4-(2-methoxyphenyl)thiazol-2-yl)carbamoyl)pyridin-2-yl) piperidine-4-carboxylic Acid $^1$H-NMR (400 MHz, DMSO-d$_6$): δ=13.24 (s, 1H), 12.28 (s, 1H), 8.89 (d, 1H), 8.20 (dd, 1H), 7.57 (dd, 1H), 7.51 (m, 1H), 7.21 (d, 1H), 7.10 (t, 1H), 6.95 (d, 1H), 4.36 (d, 2H), 3.86 (s, 3H), 3.12 (t, 2H), 2.57 (m, 1H), 1.90 (d, 2H), 1.51 (dd, 2H).

HPLC-MS: Rt 2.378, m/z 464.1 (MH$^+$).

Example 3: 1-(5-((5-cyano-4-(3-methoxyphenyl)thiazol-2-yl)carbamoyl)pyridin-2-yl) piperidine-4-carboxylic Acid $^1$H-NMR (400 MHz, DMSO-d$_6$): δ=13.32 (s, 1H), 8.88 (d, 1H), 8.23 (m, 1H), 7.62 (dd, 1H), 7.57 (d, 1H), 7.50 (t, 1H), 7.12 (dd, 1H), 7.02 (d, 1H), 4.36 (d, 2H), 3.83 (s, 3H), 3.16 (t, 2H), 2.60 (t, 1H), 1.91 (d, 2H), 1.54 (dd, 2H).

HPLC-MS: Rt 3.474 m/z 464.0 (MH$^+$).

Example 4: 1-(5-(5-cyano-4-(4-methoxyphenyl)thiazol-2-ylcarbamoyl)pyridin-2-yl) piperidine-4-carboxylic Acid $^1$H-NMR (400 MHz, DMSO-d$_6$): δ=13.24 (s, 1H), 12.31 (s, 1H), 8.88 (d, 1H), 8.20 (dd, 1H), 8.01 (d, 2H), 7.14 (d, 2H), 6.95 (d, 1H), 4.36 (d, 2H), 3.84 (s, 3H), 3.11 (t, 2H), 2.58 (m, 1H), 1.90 (d, 2H), 1.51 (dd, 2H).

HPLC-MS: Rt 3.028, m/z 364.1 (MH$^+$).

Example 5: 1-(5-((5-cyano-4-(2-fluorophenyl)thiazol-2-yl)carbamoyl)pyridin-2-yl) piperidine-4-carboxylic Acid $^1$H-NMR (400 MHz, DMSO-de): δ=13.34 (s, 1H), 8.89 (d, 1H), 8.20 (dd, 1H), 7.76 (td, 1H), 7.62 (m, 1H), 7.43 (m, 2H), 6.96 (d, 1H), 4.36 (d, 2H), 3.12 (m, 2H), 2.59 (m, 1H), 1.90 (dd, 2H), 1.51 (m, 2H).

HPLC-MS: Rt 2.998, m/z 452.1 (MH$^+$).

Example 6: 1-(5-((5-cyano-4-(3-fluorophenyl)thiazol-2-yl)carbamoyl)pyridin-2-yl) piperidine-4-carboxylic Acid $^1$H-NMR (400 MHz, DMSO-d$_6$): δ=13.41 (s, 1H), 8.88 (d, 1H), 8.25 (dd, 1H), 7.89 (m, 1H), 7.78 (m, 1H), 7.65 (m, 1H), 7.41 (td, 1H), 7.07 (d, 1H), 4.36 (d, 2H), 3.19 (m, 2H), 2.62 (m, 1H), 1.92 (dd, 2H), 1.55 (m, 2H).

HPLC-MS: Rt 3.209, m/z 452.1 (MH$^+$).

Example 7: 1-(5-((5-cyano-4-(4-fluorophenyl)thiazol-2-yl)carbamoyl)pyridin-2-yl) piperidine-4-carboxylic Acid $^1$H-NMR (400 MHz, DMSO-d$_6$): δ=13.41 (s, 1H), 8.88 (d, 1H), 8.25 (dd, 1H), 8.08 (m, 2H), 7.44 (t, 2H), 7.08 (d, 1H), 4.36 (d, 2H), 3.19 (t, 2H), 2.62 (m, 1H), 1.92 (dd, 2H), 1.55 (m, 2H).
HPLC-MS: Rt 3.221, m/z 452.1 (MH+).

Example 8: 1-(5-((4-(2-chlorophenyl)-5-cyanothiazol-2-yl)carbamoyl)pyridin-2-yl) piperidine-4-carboxylic Acid ¹H-NMR (400 MHz, DMSO-d₆): δ=13.33 (s, 1H), 12.30 (s, 1H), 8.88 (d, 1H), 8.20 (dd, 1H), 7.66 (m, 2H), 7.55 (d, 2H), 6.96 (d, 1H), 4.36 (d, 2H), 3.12 (t, 2H), 2.59 (d, 1H), 1.90 (d, 2H), 1.51 (m, 2H).
HPLC-MS: Rt 2.755; m/z 469.1 (MH+).

Example 9: 1-(5-((5-cyano-4-(pyridin-2-yl)thiazol-2-yl)carbamoyl)pyridin-2-yl) piperidine-4-carboxylic Acid ¹H-NMR (400 MHz, DMSO-d₆): δ=13.31 (s, 1H), 12.34 (s, 1H), 8.89 (s, 1H), 8.74 (d, 1H), 8.20 (d, 1H), 8.10 (d, 1H), 8.02 (m, 1H), 7.53 (s, 1H), 6.96 (d, 1H), 4.37 (d, 2H), 3.11 (t, 2H), 2.62 (m, 1H), 1.90 (d, 2H), 1.51 (dd, 2H).
HPLC-MS: Rt 2.657, m/z 435.1 (MH+).

Example 10: 1-(5-((5-cyano-4-(pyridin-3-yl)thiazol-2-yl)carbamoyl)pyridin-2-yl) piperidine-4-carboxylic Acid ¹H-NMR (400 MHz, DMSO-d₆): δ=13.35 (s, 1H), 12.31 (s, 1H), 9.18 (s, 1H), 8.88 (s, 1H), 8.72 (d, 1H), 8.35 (d, 1H), 8.20 (d, 1H), 7.63 (dd, 1H), 6.95 (d, 1H), 4.36 (d, 2H), 3.11 (t, 2H), 2.59 (m, 1H), 1.90 (d, 2H), 1.51 (dd, 2H).
HPLC-MS: Rt 2.648, m/z 435.0 (MH+).

Example 11: 1-(5-(5-cyano-4-(pyridin-4-yl)thiazol-2-ylcarbamoyl)pyridin-2-yl) piperidine-4-carboxylic Acid ¹H-NMR (400 MHz, DMSO-d₆): δ=13.36 (s, 1H), 12.29 (s, 1H), 8.88 (s, 1H), 8.81 (d, 1H), 8.19 (d, 1H), 7.94 (d, 1H), 6.94 (d, 1H), 4.36 (d, 2H), 3.12 (t, 2H), 2.58 (m, 1H), 1.90 (d, 2H), 1.52 (dd, 2H).
HPLC-MS: Rt 2.556, m/z 435.1 (MH+).

Example 12: 1-(5-(5-cyano-4-(6-methoxypyridin-3-yl)thiazol-2-ylcarbamoyl)pyridin-2-yl) piperidine-4-carboxylic Acid ¹H-NMR (400 MHz, DMSO-d₆): δ=13.27 (s, 1H), 12.28 (s, 1H), 8.83 (d, 1H), 8.82 (d, 1H), 8.27 (dd, 1H), 8.19 (dd, 1H), 7.04 (d, 1H), 6.99 (d, 1H), 4.36 (d, 2H), 3.94 (s, 3H), 3.12 (t, 2H), 2.57 (m, 1H), 1.90 (d, 2H), 1.52 (dd, 2H).
HPLC-MS: Rt 2.705, m/z 465.1 (MH+).

Example 13: 1-(5-(5-cyano-4-(furan-2-yl)thiazol-2-ylcarbamoyl)pyridin-2-yl) piperidine-4-carboxylic Acid ¹H-NMR (400 MHz, DMSO-d₆): δ=13.30 (s, 1H), 12.28 (s, 1H), 8.88 (d, 1H), 8.19 (dd, 1H), 7.98 (s, 1H), 7.09 (d, 1H), 6.94 (d, 1H), 6.74 (d, 1H), 4.36 (d, 2H), 3.12 (t, 2H), 2.59 (m, 1H), 1.90 (d, 2H), 1.52 (dd, 2H).
HPLC-MS: Rt 2.277, m/z 424.0 (MH+).

Example 14: 1-(5-(5-cyano-4-(thiophen-2-yl)thiazol-2-ylcarbamoyl)pyridin-2-yl) piperidine-4-carboxylic Acid ¹H-NMR (400 MHz, DMSO-d₆): δ=13.27 (s, 1H), 12.28 (s, 1H), 8.88 (d, 1H), 8.20 (dd, 1H), 7.91 (dd, 1H), 7.82 (dd, 1H), 7.28 (dd, 1H), 6.94 (d, 2H), 4.36 (d, 2H), 3.12 (t, 2H), 2.57 (m, 1H), 1.90 (d, 2H), 1.52 (dd, 2H).
HPLC-MS: Rt 2.483, m/z 440.0 (MH+).

Example 15: 1-(5-(5-cyano-4-(thiophen-3-yl)thiazol-2-ylcarbamoyl)pyridin-2-yl) piperidine-4-carboxylic Acid ¹H-NMR (400 MHz, DMSO-d₆): δ=13.40 (s, 1H), 8.87 (d, 1H), 8.25 (dd, 1H), 8.21 (dd, 1H), 7.77 (m, 2H), 7.09 (d, 1H), 4.36 (d, 2H), 3.19 (ddd, 2H), 2.63 (m, 1H), 1.92 (dd, 2H), 1.56 (m, 2H).
HPLC-MS: Rt 3.043, m/z 440.0 (MH+).

Example 16: 1-(5-((4-(4-chlorothiophen-2-yl)-5-cyanothiazol-2-yl)carbamoyl)pyridin-2-yl) piperidine-4-carboxylic Acid ¹H-NMR (400 MHz, DMSO-d₆): δ=13.29 (s, 1H), 12.27 (s, 1H), 8.87 (s, 1H), 8.18 (d, 1H), 7.86 (s, 1H), 7.73 (s, 1H), 6.93 (d, 1H), 4.36 (d, 2H), 3.12 (t, 2H), 2.59 (m, 1H), 1.90 (d, 2H), 1.52 (dd, 2H).
HPLC-MS: Rt 3.221, m/z 474.0 (MH+).

Example 17: 1-(5-(5-cyano-4-(thiazol-2-yl)thiazol-2-ylcarbamoyl)pyridin-2-yl) piperidine-4-carboxylic Acid ¹H-NMR (400 MHz, DMSO-d₆): δ=13.36 (s, 1H), 12.28 (s, 1H), 8.89 (d, 1H), 8.20 (dd, 1H), 8.12 (d, 1H), 8.02 (d, 1H), 6.95 (d, 1H), 4.36 (d, 2H), 3.12 (t, 2H), 2.59 (m, 1H), 1.90 (d, 2H), 1.52 (dd, 2H).
HPLC-MS: Rt 2.474, m/z 441.0 (MH+).

The invention claimed is:

1. A compound of formula (I):

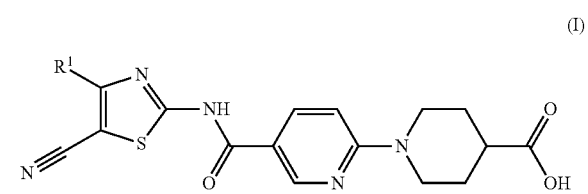

wherein:
R¹ represents a phenyl group or a five or six-membered heteroaryl group with one, two or three heteroatoms selected from the group consisting of O, S and N, which group is optionally substituted by 1, 2 or 3 substituents selected from the group consisting of halogen atom, $C_1$-$C_6$ haloalkyl linear or branched, $C_1$-$C_6$ alkyl linear or branched, $C_1$-$C_6$ alkoxy linear or branched and cyano group,
or pharmaceutically acceptable salts thereof.

2. The compound according to claim 1 wherein R¹ represents a five or six-membered heteroaryl group with one, two or three heteroatoms selected from the group consisting of O, S and N, which group is optionally substituted by 1, 2 or 3 substituents selected from the group consisting of halogen atom, $C_1$-$C_6$ haloalkyl linear or branched, $C_1$-$C_6$ alkyl linear or branched, $C_1$-$C_6$ alkoxy linear or branched and cyano group, or pharmaceutically acceptable salts thereof.

3. The compound according to claim 2 wherein R¹ represents a group selected from the group consisting of thienyl, furyl, pyridyl and thiazolyl optionally substituted by 1, 2 or 3 substituents selected from the group consisting of halogen atom, $C_1$-$C_6$ alkyl linear or branched, $C_1$-$C_6$ alkoxy linear or branched and cyano group, or pharmaceutically acceptable salts thereof.

4. The compound according to claim 3 wherein $R^1$ represents a thienyl group optionally substituted by 1, 2 or 3 substituents selected from the group consisting of halogen atom and $C_1$-$C_6$ alkoxy linear or branched, or pharmaceutically acceptable salts thereof.

5. The compound according to claim 3 wherein $R^1$ represents a phenyl group optionally substituted by 1 or 2 substituents selected from the group consisting of halogen atom and $C_1$-$C_6$ alkoxy linear or branched, or pharmaceutically acceptable salts thereof.

6. The compound according to claim 1 which is:
1-(5-(5-cyano-4-phenylthiazol-2-ylcarbamoyl)pyridin-2-yl)piperidine-4-carboxylic acid,
1-(5-((5-cyano-4-(2-methoxyphenyl)thiazol-2-yl)carbamoyl)pyridin-2-yl)piperidine-4-carboxylic acid,
1-(5-((5-cyano-4-(3-methoxyphenyl)thiazol-2-yl)carbamoyl)pyridin-2-yl)piperidine-4-carboxylic acid,
1-(5-(5-cyano-4-(4-methoxyphenyl)thiazol-2-ylcarbamoyl)pyridin-2-yl)piperidine-4-carboxylic acid,
1-(5-((5-cyano-4-(2-fluorophenyl)thiazol-2-yl)carbamoyl)pyridin-2-yl)piperidine-4-carboxylic acid,
1-(5-((5-cyano-4-(3-fluorophenyl)thiazol-2-yl)carbamoyl)pyridin-2-yl)piperidine-4-carboxylic acid,
1-(5-((5-cyano-4-(4-fluorophenyl)thiazol-2-yl)carbamoyl)pyridin-2-yl)piperidine-4-carboxylic acid,
1-(5-((4-(2-chlorophenyl)-5-cyanothiazol-2-yl)carbamoyl)pyridin-2-yl)piperidine-4-carboxylic acid,
1-(5-((5-cyano-4-(pyridin-2-yl)thiazol-2-yl)carbamoyl)pyridin-2-yl)piperidine-4-carboxylic acid,
1-(5-((5-cyano-4-(pyridin-3-yl)thiazol-2-yl)carbamoyl)pyridin-2-yl)piperidine-4-carboxylic acid,
1-(5-(5-cyano-4-(pyridin-4-yl)thiazol-2-ylcarbamoyl)pyridin-2-yl)piperidine-4-carboxylic acid,
1-(5-(5-cyano-4-(6-methoxypyridin-3-yl)thiazol-2-ylcarbamoyl)pyridin-2-yl)piperidine-4-carboxylic acid,
1-(5-(5-cyano-4-(furan-2-yl)thiazol-2-ylcarbamoyl)pyridin-2-yl)piperidine-4-carboxylic acid,
1-(5-(5-cyano-4-(thiophen-2-yl)thiazol-2-ylcarbamoyl)pyridin-2-yl)piperidine-4-carboxylic acid,
1-(5-(5-cyano-4-(thiophen-3-yl)thiazol-2-ylcarbamoyl)pyridin-2-yl)piperidine-4-carboxylic acid,
1-(5-((4-(4-chlorothiophen-2-yl)-5-cyanothiazol-2-yl)carbamoyl)pyridin-2-yl)piperidine-4-carboxylic acid, or
1-(5-(5-cyano-4-(thiazol-2-yl)thiazol-2-ylcarbamoyl)pyridin-2-yl)piperidine-4-carboxylic acid, or pharmaceutically acceptable salts thereof.

7. A pharmaceutical composition comprising a compound as defined in claim 1 or pharmaceutically acceptable salt thereof and a pharmaceutically acceptable diluent or carrier.

8. A method for the treatment of a disease or pathological condition susceptible to amelioration by modulation of the adenosine $A_3$ receptor in a subject comprising administering to the subject in need thereof an effective amount of a compound according to claim 1, wherein the disease or pathological condition susceptible to amelioration by modulation of the adenosine $A_3$ receptor is at least one disease or condition selected from the group consisting of atherosclerosis, asthma, prostate cancer, acute renal failure, rheumatoid arthritis, psoriasis, immune thrombocytopenia, Crohn's disease, colitis, irritable bowel syndrome, glaucoma, dry eye syndrome, uveitis and neuropathic pain.

9. A combination comprising a compound according to claim 1 and a therapeutic agent used for the treatment of a disease or condition selected from the group consisting of atherosclerosis, asthma, prostate cancer, acute renal failure, rheumatoid arthritis, psoriasis, immune thrombocytopenia, Crohn's disease, colitis, irritable bowel syndrome, glaucoma, dry eye syndrome, uveitis and neuropathic pain.

10. A combination comprising a compound according to claim 1 and a therapeutic agent selected from the group consisting of atorvastatin, rosuvastatin, simvastatin, Montelukast, Bicalutamide, Flutamide, Tofacitinib, Hydrochlorothiazide and Lubiprostone.

11. A method for the treatment of atherosclerosis, asthma, prostate cancer, acute renal failure, rheumatoid arthritis, psoriasis, immune thrombocytopenia, Crohn's disease, colitis, irritable bowel syndrome, glaucoma, dry eye syndrome, uveitis or neuropathic pain in a subject comprising administering to the subject in need thereof an effective amount of a compound according to claim 1 and a therapeutic agent used for the treatment of atherosclerosis, asthma, prostate cancer, acute renal failure, rheumatoid arthritis, psoriasis, immune thrombocytopenia, Crohn's disease, colitis, irritable bowel syndrome, glaucoma, dry eye syndrome, uveitis or neuropathic pain.

12. The method of claim 11, wherein the therapeutic agent is atorvastatin, rosuvastatin, simvastatin, Montelukast, Bicalutamide, Flutamide, Tofacitinib, Hydrochlorothiazide or Lubiprostone.

* * * * *